US012004995B2

(12) United States Patent
Ghebremeskel et al.

(10) Patent No.: US 12,004,995 B2
(45) Date of Patent: Jun. 11, 2024

(54) INTRAOCULAR IMPLANT WITH HIGH LOADING OF A PROSTAMIDE

(71) Applicant: Allergan, Inc., North Chicago, IL (US)

(72) Inventors: Alazar N. Ghebremeskel, Irvine, CA (US); Jinping Wan, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 17/443,083

(22) Filed: Jul. 20, 2021

(65) Prior Publication Data

US 2022/0023095 A1    Jan. 27, 2022

Related U.S. Application Data

(60) Provisional application No. 63/054,620, filed on Jul. 21, 2020.

(51) Int. Cl.
| | | |
|---|---|---|
| *A61K 9/00* | (2006.01) | |
| *A61F 9/00* | (2006.01) | |
| *A61F 9/007* | (2006.01) | |
| *A61K 31/559* | (2006.01) | |
| *A61K 47/34* | (2017.01) | |
| *A61P 27/06* | (2006.01) | |
| *C08L 67/04* | (2006.01) | |

(52) U.S. Cl.
CPC ........ *A61F 9/0017* (2013.01); *A61F 9/00781* (2013.01); *A61K 9/0051* (2013.01); *A61K 31/559* (2013.01); *A61K 47/34* (2013.01); *C08L 67/04* (2013.01); *A61F 2210/0004* (2013.01)

(58) Field of Classification Search
CPC ................ A61F 9/0017; A61F 9/00781; A61F 2210/0004; A61K 9/0051; A61K 31/559; A61K 47/24; C08L 67/04; A61P 27/06
See application file for complete search history.

(56) References Cited

U.S. PATENT DOCUMENTS

| | | | |
|---|---|---|---|
| 5,741,810 A | 4/1998 | Burk | |
| 5,834,498 A | 11/1998 | Burk | |
| 6,124,344 A | 9/2000 | Burk | |
| 6,602,900 B2 | 8/2003 | Burk | |
| 6,899,717 B2 | 5/2005 | Weber et al. | |
| 8,974,812 B2 | 3/2015 | Nivaggioli et al. | |
| 9,289,413 B2 * | 3/2016 | Hughes | A61K 9/0051 |
| 9,492,316 B2 * | 11/2016 | Ghebremeskel | A61P 27/06 |
| 9,889,142 B2 | 2/2018 | Hughes et al. | |
| 9,980,974 B2 * | 5/2018 | Ghebremeskel | A61K 47/10 |
| 10,765,629 B2 * | 9/2020 | Wu | A61K 47/34 |
| 2004/0054374 A1 | 3/2004 | Weber | |
| 2010/0278897 A1 | 11/2010 | Shi et al. | |
| 2014/0271780 A1 * | 9/2014 | Hughes | A61K 9/146 |
| | | | 424/428 |
| 2014/0305354 A1 | 10/2014 | Chalabi et al. | |
| 2015/0118279 A1 * | 4/2015 | Ghebremeskel | A61K 31/165 |
| | | | 424/428 |
| 2019/0192341 A1 * | 6/2019 | Robinson | A61P 27/06 |
| 2020/0170941 A1 | 6/2020 | Wu et al. | |
| 2022/0218721 A1 * | 7/2022 | Ghebremeskel | A61K 31/5575 |
| 2023/0026451 A1 * | 1/2023 | Hughes | A61K 9/204 |

FOREIGN PATENT DOCUMENTS

| | | | |
|---|---|---|---|
| WO | 2010056598 | 12/2010 | |
| WO | 2014127243 | 8/2014 | |
| WO | WO-2019023211 A1 * | 1/2019 | ........... A61K 31/559 |

OTHER PUBLICATIONS

Evonik, Resomer Bioresorbable Polymers for Controlled Release, retrieved from https://healthcare.evonik.com/product/health-care/en/products/biomaterials/resomer/pages/controlled-release.aspx, on Jan. 19, 2020, 5 pages.
Evonik, Setting the Benchmark for Biodegradable Polymers for Controlled Release, retrieved from https://healthcare.evonik.com/en/pharmaceuticals/parenteral-drug-delivery/parenteral-excipients/resomer-portfolio/standard-polymers on Mar. 18, 2021, 8 pages.
Sigma-Aldrich, Phosphate buffered saline, retrieved from https://www.sigmaaldrich.com/catalog/product/sigma/p5368?lang=en&region=US, on Jul. 8, 2020, 4 pages.
Sigma-Aldrich, Resomer®—Biodegradable Polymers for Sutures, Medical Devices, Drug Delivery Systems and Tissue Engineering, retrieved from https://www.sigmaaldrich.com/technical-documents/articles/material-matters/resomer-biod., on Jun. 29, 2018, 3 pages.
Sigma-Aldrich, Resomer® Biodegradable Polymers for Medical Device Applications Research, retrieved from https://www.sigmaaldrich.com/technical-documents/articles/materials-science/polymer-sci., on Jun. 29, 2018, 3 pages.
United States Pharmacopeia, The National Formulary, USP23, 1995, 1790-1798, 18.
Unknown, Phosphate-buffered saline (PBS), retrieved from cshprotocols.cshlp.org/content/2006/1/pdb.rec8247, on Jul. 8, 2020, 1 page.
International Search Report & Written Opinion dated Dec. 3, 2021, for PCT/US2021/042361, filed Jul. 20, 2021, in the name of Allergan, Inc.
Huang, Xiao, et al., On the Importance and Mechanisms of Burst Release in Matrix-Controlled Drug Delivery Systems, Journal of Controlled Release, 2001, 121-136, vol. 73, Elsevier Science B.V.
Kishida, A., et al., Polymer Drugs & Polymeric Drugs X: Slow Release of 5-Flourouracil from Biodegradable Poly(y-glutamic acid) and Its Benzyl Ester Matrices, J. Bioactive & Compatible Polymers, 1998, 271-278, 13.

* cited by examiner

*Primary Examiner* — Abigail Vanhorn
(74) *Attorney, Agent, or Firm* — Jonathan Y. Bass; Stephen C. D'Amico; Matthew O. Brady

(57) ABSTRACT

Biodegradable intraocular implants with a high loading of a prostamide compound for the immediate and sustained reduction of intraocular pressure and treatment of glaucoma in an eye of a patient are described.

6 Claims, 8 Drawing Sheets

| Timepoint | 3.8 µg/150 µm dia. | 7.5 µg /150 µm dia. |
| --- | --- | --- |
| | Implant 1 | Implant 5 |
| Day 0 | | |
| Day 91 | | |
| Day 127 | | |
| Day 196 | | |
| Day 280 | | |
| Day 415 | | N/A |

FIG. 7

INTRAOCULAR IMPLANT WITH HIGH LOADING OF A PROSTAMIDE

CROSS-REFERENCE TO RELATED APPLICATIONS

This application claims the benefit under 35 USC 119(e) of U.S. provisional patent application 63/054,620 filed Jul. 21, 2021, the entire content of which is herein incorporated by reference in its entirety.

FIELD

Described herein are intraocular implants with high loading of a prostamide. In particular, described herein are devices and methods to treat an eye of a patient, and more specifically to intraocular implants that provide extended release of a therapeutic agent to an eye in which the implant is placed to treat ocular hypertension, such as by reducing or at least maintaining intraocular pressure (IOP), and to methods of making and using such implants.

BACKGROUND

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye often characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The increased intraocular tension in glaucoma is due to the obstruction of aqueous humor outflow. In chronic open-angle glaucoma, the anterior chamber and its anatomic structures appear essentially normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Reduction of intraocular pressure may help to prevent glaucoma or loss of vision due to glaucoma. Currently, eye drops containing therapeutically active agents for reducing intraocular pressure are given to many patients, who may take the drops one or more times a day to reduce elevated intraocular pressure associated with glaucoma.

It would be advantageous to provide eye implantable drug delivery systems, such as intraocular implants, and methods of using such systems, that are capable of releasing a therapeutic agent, such as a hypotensive (or IOP-lowering) agent, at a sustained or controlled rate for extended periods of time and in amounts (i.e., extended release rather than burst release) with few or absent negative side effects to thereby reduce intraocular pressure in an eye of a patient, including but not limited to patients suffering from or at risk of developing glaucoma. The therapeutic agent can be delivered in the intracameral space or into the vitreous humor where it can be effective at the anterior or posterior segments of the human eye. It would also be advantageous to obtain a linear drug release profile for extended periods of time. An implant delivery system with relatively high loading would be desirable because the size of the implant can be reduced without decreasing the effective amount of the drug delivered.

Additional parameters to consider when formulating the implant delivery system include rate and extent of release of drug from the sustained release implant, the extent to which a sustained release implant swells when placed in aqueous media (compared to initial size), and biodegradation time of the implant after drug release is completed.

To minimize implant mass, dimensions, and injection frequency, there exists a need to simultaneously maximize drug loading, the polymer erosion rate, and the duration of drug release time. This is often difficult to achieve in practice, as typically optimizing one component/factor compromises the others.

SUMMARY

The present disclosure is related to extended, long term reduction of intraocular pressure in the eye which is provided by intraocular administration of one or more of the biodegradable intraocular implants. The biodegradable intraocular implant comprises or consists of a biodegradable polymer material and a therapeutic agent associated with the biodegradable polymer material. The implant(s) can be administered to the eye as monotherapy and can provide the therapeutic agent directly to an ocular region of the eye in an amount effective for reducing elevated intraocular pressure (ocular hypertension) in the eye for an extended period. The implants can also be used to treat or prevent glaucoma or other medical conditions of the eye associated with elevated intraocular pressure.

The therapeutic agent contained by the intraocular implant of the present disclosure can comprise, consist essentially of, or consist of, a compound that is effective in reducing intraocular pressure in a hypertensive eye. In some embodiments, the therapeutic agent comprises or consists of Compound 1:

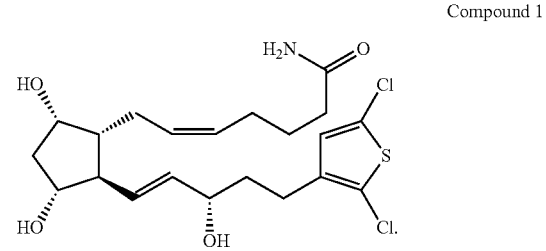 [SMILES: NC(=O)CCC/C=C\C[C@@H]1[C@@H](/C=C/[C@@H](O)CCc2cc(Cl)sc2Cl)[C@H](O)C[C@@H]1O]

Compound 1

Accordingly, the present disclosure describes a biodegradable intraocular implant effective for reducing intraocular pressure in an eye of a patient for an extended period, wherein the implant comprises or consists of a biodegradable polymer material and Compound 1, or a pharmaceutically acceptable salt thereof, and wherein Compound 1 is present in an amount of greater than 8 wt %, such as between 8 and 20 wt % (including 20 wt %, such as from 9 to 18%, from 9 to 17%, from 9 to 16%, from 9 to 15%, and from 10 to 15%), 11 wt %, 12 wt %, or 15 wt %, of the implant.

In some embodiments, the biodegradable intraocular implant comprises a biodegradable polymer material and Compound 1 as the pharmaceutically active agent, wherein the intraocular implant comprises no pharmaceutically active agent or IOP-lowering agent other than Compound 1.

Compound 1 can be associated with the biodegradable polymer material. Thus, the Compound can be mixed with, dissolved and/or dispersed within, encapsulated by, or coupled to the biodegradable polymer material. Compound 1 can be uniformly or non-uniformly dispersed within or distributed throughout the biodegradable polymer material. Release of Compound 1 from an implant following placement in an eye can occur by diffusion of Compound 1, erosion or degradation of the polymer material, dissolution, osmosis, or any combination thereof.

The biodegradable intraocular implant described herein can be specifically sized and formulated for placement in an ocular region of an eye, such as, for example, the vitreous body or anterior chamber of the eye, to treat glaucoma and reduce intraocular pressure, including, for example, elevated intraocular pressure (or ocular hypertension) in the eye.

In some embodiments, the intraocular biodegradable implant can release Compound 1 or a pharmaceutically acceptable salt thereof continuously in vitro and/or in vivo in an eye for greater than one month, such as between about 1 and about 3 months or more, for about 3 to about 6 months, or for about 6 months or more after placement in the eye of a patient.

Implants of the present disclosure are designed to release Compound 1 in a controlled fashion. In some forms, the implant will provide a linear or near constant rate of release of Compound 1 for greater than 1 month, e.g., greater than 2 months, between 1 and 3 months, for 3 to 6 months, or for 6 to 12 months or more.

One embodiment is an extruded, intracameral, biodegradable implant comprising between about 8% and about 20% (20% inclusive, such as from about 9 to about 18%, from about 9 to about 17%, from about 9 to about 16%, from about 9 to about 15%, and from about 10 to about 15%), such as about 11%, about 12%, or about 15% by weight Compound 1, and optionally from about 2% to about 6% by weight hexadecan-1-ol (hexadecanol), wherein the implant continuously releases Compound 1 for 2 to 5 months in vitro in phosphate buffered saline at 37° C.

The biodegradable intraocular implant can comprise a biodegradable polymer material and Compound 1 wherein i) Compound 1 is in an amount between about 8 and about 20% (20% inclusive, such as from about 9 to about 18%, from about 9 to about 17%, from about 9 to about 16%, from about 9 to about 15%, and from about 10 to about 15%) by weight of the implant, ii) the implant releases Compound 1 continuously in vitro and/or in vivo in an eye for greater than one month, and iii) the implant does not comprise polyethylene glycol.

In some forms of this implant, the biodegradable polymer material comprises a poly(D,L-lactide) having an acid end group and an inherent viscosity of 0.16-0.24 dl/g (Polymer 1), and a poly(D,L-lactide) having an ester end group and an inherent viscosity of 0.25-0.35 dl/g (Polymer 2), and a poly(D,L-lactide-co-glycolide) copolymer having an ester end group, a D,L-lactide to glycolide molar ratio of about 75:25 (e.g., from 73:27 to 77:23), and an inherent viscosity of 0.16-0.24 dl/g (Polymer 3), wherein the inherent viscosity of each polymer and copolymer is measured for a 0.1% solution of the polymer or copolymer in chloroform at 25° C. In some forms of this implant, Polymer 1 is present in an amount of about 0 to about 20 wt % (such as about 4 to about 10 wt % or about 4 to about 20 wt %, e.g. about 4, about 5, about 6, about 7, about 8, about 9, about 10, about 11, about 12, about 13, about 14, about 15, about 16, about 17, about 18, or about 20 wt %). In some forms of this implant, Polymer 2, in an amount less than that of Polymer 3, is present in an amount of about 20 to about 40 wt % (such as about 20 to about 30 wt %, e.g. about 20, about 25, about 30, about 35, or about 40 wt %). In some forms of this implant, Polymer 3 is present in an amount of about 30 to about 70 wt % (such as about 35 to about 50 wt %, e.g. about 30, about 35, about 40, about 45 wt %). In some form of this implant, the weight ratio of Polymer 2 versus Polymer 3 is 2:5 to 4:3, such as 1:2 to 1:1, 1:2, 5:9, 5:8, 2:3, 3:4, 6:7, or 1:1.

The biodegradable implant can be formulated to comprise at least about 3 to about 10 µg (e.g., about 5 or about 7.5 µg) of Compound 1 in an about 100 to about 200 µm diameter implant (e.g., an about 150 µm diameter implant).

One embodiment provides for a method of reducing intraocular pressure in a patient in need thereof comprising administering to the eye(s) of the patient a pharmaceutical composition, the composition comprising a therapeutically effective amount of Compound 1 or a pharmaceutically acceptable salt thereof. Some embodiments provide for a method of reducing intraocular pressure in a patient in need thereof comprising administering to the eye(s) of the patient a pharmaceutical composition comprising a therapeutically effective amount of Compound 1. The pharmaceutical composition for reducing intraocular pressure will generally be biocompatible with the eye and will contain a therapeutically effective amount of Compound 1 and a pharmaceutically acceptable excipient. Biocompatible implants and polymers produce few or no toxic effects, are not injurious or physiologically reactive, and do not cause an immunological reaction.

Other embodiments provide for a method of making biodegradable intraocular implants effective for reducing intraocular pressure in a patient, the implant comprising or consisting of a therapeutic agent, a biodegradable polymer material, and, optionally, one or more excipients, the method comprising in order a) blending the therapeutic agent with a biodegradable polymer or two or more biodegradable polymers and one or more excipients, if any, to form a mixture, b) extruding the mixture to form a filament, and c) cutting the filament to lengths suitable for placement in an eye of a patient suffering from elevated intraocular, thereby forming the intraocular implants. In particular embodiments the filament is cut to lengths suitable for placement in the anterior chamber of an eye. The therapeutic agent can comprise Compound 1 as defined herein. In some instances the therapeutic agent used for blending with the polymer(s) (step a) can be in the form of a solid. The mixture can be extruded at a temperature of from about 60° C. to about 150° C.

Yet other embodiments provide for an apparatus for implanting or injecting a biodegradable intraocular implant, according to any of the embodiments described herein, into an ocular region of an eye in a patient suffering from glaucoma or ocular hypertension (i.e., elevated intraocular pressure), the apparatus comprising an elongate housing having a longitudinal axis and a cannula extending longitudinally from the housing, the cannula having a lumen extending therethrough, the lumen configured to receive an intraocular implant, the apparatus further comprising an intraocular implant according to any of the embodiments described herein. The implant can be located within the cannula lumen or in a position proximal to the cannula lumen. In specific forms of the apparatus the dimensions of the cannula are identical to that or not greater than that of a 21, 22, 25, 27, 28, or 30 gauge needle and the cannula will have a beveled or sharp tip to facilitate the penetration of ocular tissue. In some forms, the outer and inner diameters of the cannula are not greater than those of a 25 or 27 gauge needle.

Also within the scope of this disclosure are methods for delivering the intraocular implant into the eye of a patient suffering from glaucoma or elevated intraocular pressure using an apparatus as described above, the apparatus comprising a cannula having a proximal end, a distal sharp end, and a lumen extending therethrough, an intraocular implant selected from any of those described herein, and an actuator, the movement of which causes the implant to be ejected from the apparatus, the cannula lumen sized to receive the intraocular implant and permit translation of the implant therethrough, the method comprising the steps of inserting the cannula into an ocular region of a patient's eye, and depressing or activating the actuator, thereby ejecting the implant from the cannula into the patient's eye. In some embodiments the ocular region of the eye into which the implant is injected can be the anterior chamber or vitreous body of the eye.

Some non-limiting example embodiments are given below.

Example Embodiment 1

A biodegradable intraocular implant comprising a biodegradable polymer material and Compound 1:

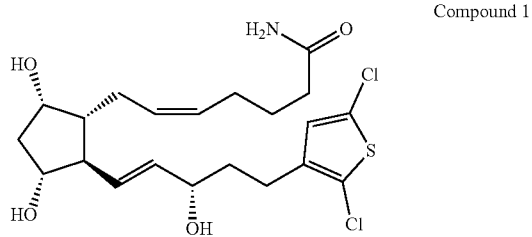 [SMILES: NC(=O)CCC/C=C\C[C@@H]1[C@@H](/C=C/[C@@H](O)CCc2cc(Cl)sc2Cl)[C@H](O)C[C@@H]1O]

Compound 1 wherein Compound 1 is in an amount between 10 and 20% by weight of the implant and wherein the implant continuously releases Compound 1 for 2 to 6 months in vitro.

Example Embodiment 2

A biodegradable intraocular implant comprising a biodegradable polymer material and Compound 1:

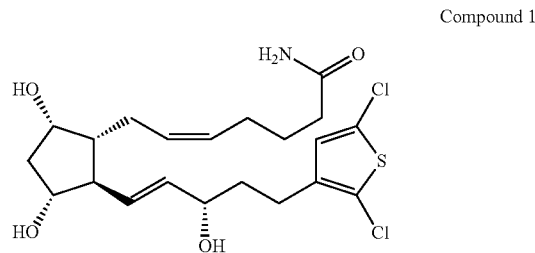 [SMILES: NC(=O)CCC/C=C\C[C@@H]1[C@@H](/C=C/[C@@H](O)CCc2cc(Cl)sc2Cl)[C@H](O)C[C@@H]1O]

Compound 1 wherein Compound 1 is in an amount between 10 and 20% by weight of the implant and wherein the implant releases in vitro less than 30% of Compound 1 during the first 24 hours.

Example Embodiment 3

The biodegradable intraocular implant of example embodiment 2, wherein the implant releases in vitro less than 35% of Compound 1 during the first 24 hours.

Example Embodiment 4

The biodegradable intraocular implant of example embodiment 2, wherein the implant releases in vitro less than 20% of Compound 1 during the first 24 hours.

Example Embodiment 5

The biodegradable intraocular implant of example embodiment 2, wherein the implant releases in vitro less than 15% of Compound 1 during the first 24 hours.

Example Embodiment 6

The biodegradable intraocular implant of any one of the preceding example embodiments, wherein the in vitro release of Compound 1 is measured in a phosphate buffered saline (PBS) solution at a pH of 7.4±0.05 and at 37° C., and wherein the PBS solution is a PBS solution that is free of magnesium and calcium and has a pH of 7.4±0.05 at 25° C.

Example Embodiment 7

A biodegradable intraocular implant comprising a biodegradable polymer material and Compound 1:

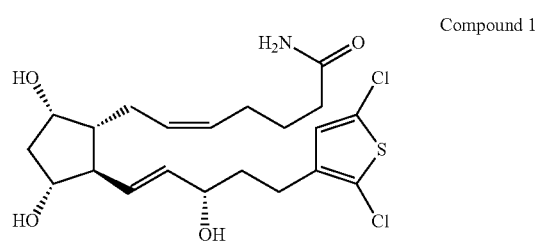 [SMILES: NC(=O)CCC/C=C\C[C@@H]1[C@@H](/C=C/[C@@H](O)CCc2cc(Cl)sc2Cl)[C@H](O)C[C@@H]1O]

Compound 1 wherein i) Compound 1 is in an amount between 10 and 20% by weight of the implant, ii) the implant releases Compound 1 continuously in vitro and/or in vivo in an eye for greater than one month, and iii) the implant does not comprise polyethylene glycol.

Example Embodiment 8

The biodegradable intraocular implant of any one of the preceding example embodiments, wherein the biodegradable polymer material comprises a first polymer that is poly(D,L-lactide) having an acid end group and an inherent viscosity of about 0.16-0.24 dl/g, a second polymer that is poly(D,L-lactide) having an ester end group and an inherent viscosity of about 0.25-0.35 dl/g, and a third polymer that is poly(D,L-lactide-co-glycolide) having an ester end group and an inherent viscosity of about 0.16-0.24 dl/g and a D,L-lactide:glycolide ratio of about 75:25, wherein the inherent viscosity of each polymer and copolymer is measured for a 0.1% solution of the polymer or copolymer in chloroform at 25° C.

Example Embodiment 9

A biodegradable intraocular implant comprising a biodegradable polymer material and Compound 1:

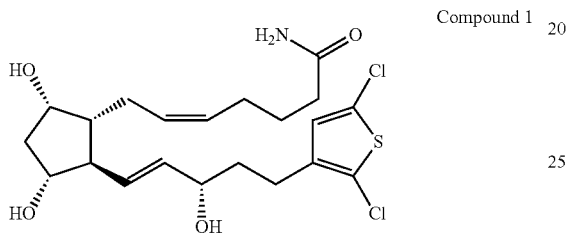

Compound 1 wherein i) Compound 1 is in an amount between 10 and 20% by weight of the implant, ii) the biodegradable polymer material comprises a first polymer that is poly(D,L-lactide) having an acid end group and an inherent viscosity of about 0.16-0.24 dl/g, a second polymer that is poly(D,L-lactide) having an ester end group and an inherent viscosity of about 0.25-0.35 dl/g, and a third polymer that is poly(D,L-lactide-co-glycolide) having an ester end group and an inherent viscosity of about 0.16-0.24 dl/g and a D,L-lactide:glycolide ratio of about 75:25, wherein the inherent viscosity of each polymer and copolymer is measured for a 0.1% solution of the polymer or copolymer in chloroform at 25° C., and (iii) the second polymer, in an amount less than or equal to that of the third polymer, is present in an amount of 20-40 wt %.

Example Embodiment 10

A biodegradable intraocular implant comprising a biodegradable polymer material and Compound 1:

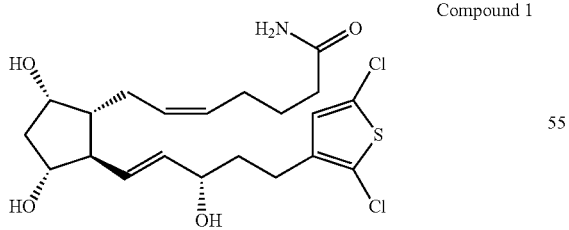

Compound 1 wherein i) Compound 1 is in an amount between 10 and 20% by weight of the implant, ii) the biodegradable polymer material comprises a first polymer that is poly(D,L-lactide) having an acid end group and an inherent viscosity of about 0.16-0.24 dl/g, a second polymer that is poly(D,L-lactide) having an ester end group and an inherent viscosity of about 0.25-0.35 dl/g, and a third polymer that is poly(D,L-lactide-co-glycolide) having an ester end group and an inherent viscosity of about 0.16-0.24 dl/g and a D,L-lactide:glycolide ratio of about 75:25, wherein the inherent viscosity of each polymer and copolymer is measured for a 0.1% solution of the polymer or copolymer in chloroform at 25° C., and (iii) the weight ratio of the second polymer versus the third polymer is 2:5 to 4:3.

Example Embodiment 11

The biodegradable intraocular implant of example embodiment 10, wherein the third polymer is present in an amount of about 30-70 wt %.

Example Embodiment 12

The biodegradable intraocular implant of example embodiment 10 or 11, wherein the first polymer is present in an amount of about 4-20 wt %.

Example Embodiment 13

The biodegradable intraocular implant of any one of example embodiments 9 to 12, wherein the implant releases in vitro less than 30% of Compound 1 during the first 24 hours.

Example Embodiment 14

The biodegradable intraocular implant of example embodiment 13, wherein the implant releases in vitro less than 25% of Compound 1 during the first 24 hours.

Example Embodiment 15

The biodegradable intraocular implant of example embodiment 13, wherein the implant releases in vitro less than 20% of Compound 1 during the first 24 hours.

Example Embodiment 16

The biodegradable intraocular implant of example embodiment 13, wherein the implant releases in vitro less than 15% of Compound 1 during the first 24 hours.

Example Embodiment 17

The biodegradable intraocular implant of any of the preceding example embodiments, wherein the implant further comprises cetyl alcohol.

Example Embodiment 18

The biodegradable intraocular implant of any of the preceding example embodiments, wherein the implant further comprises butylated hydroxyanisole.

Example Embodiment 19

The biodegradable intraocular implant of any of the preceding example embodiments, wherein Compound 1 is present in an amount of 11, 12, or 15 wt % of the implant.

Example Embodiment 20

The biodegradable intraocular implant of any one of the preceding example embodiments, comprising about 12% by weight of Compound 1:

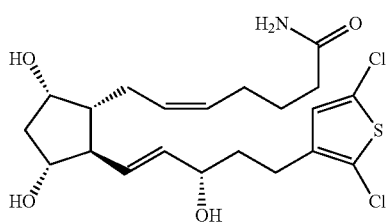

Compound 1 about 16% by weight of a first polymer that is poly(D,L-lactide) having an acid end group and an inherent viscosity of about 0.16-0.24 dl/g, about 25% by weight of a second polymer that is poly(D,L-lactide) having an ester end group and an inherent viscosity of about 0.25-0.35 dl/g, about 40% by weight of a third polymer that is poly(D,L-lactide-co-glycolide) having an ester end group and an inherent viscosity of about 0.16-0.24 dl/g and a D,L-lactide:glycolide ratio of about 75:25, about 5% by weight cetyl alcohol, and about 2% by weight butylated hydroxyanisole, wherein the inherent viscosities of the first, second, and third polymers correspond to those measured for a 0.1% solution of the polymer in chloroform at 25° C.

Example Embodiment 21

The biodegradable intraocular implant of any one of the preceding example embodiments, comprising about 12% by weight of Compound 1:

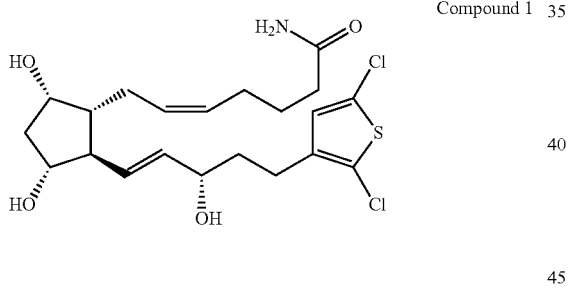

Compound 1 about 6% by weight of a first polymer that is poly(D,L-lactide) having an acid end group and an inherent viscosity of about 0.16-0.24 dl/g, about 30% by weight of a second polymer that is poly(D,L-lactide) having an ester end group and an inherent viscosity of about 0.25-0.35 dl/g, about 45% by weight of a third polymer that is poly(D,L-lactide-co-glycolide) having an ester end group and an inherent viscosity of about 0.16-0.24 dl/g and a D,L-lactide:glycolide ratio of about 75:25, about 5% by weight cetyl alcohol, and about 2% by weight butylated hydroxyanisole, wherein the inherent viscosities of the first, second, and third polymers correspond to those measured for a 0.1% solution of the polymer in chloroform at 25° C.

Example Embodiment 22

The biodegradable intraocular implant of any one of the preceding example embodiments, comprising about 15% by weight of Compound 1:

Compound 1 about 15% by weight of a first polymer that is poly(D,L-lactide) having an acid end group and an inherent viscosity of about 0.16-0.24 dl/g, about 25% by weight of a second polymer that is poly(D,L-lactide) having an ester end group and an inherent viscosity of about 0.25-0.35 dl/g, about 40% by weight of a third polymer that is poly(D,L-lactide-co-glycolide) having an ester end group and an inherent viscosity of about 0.16-0.24 dl/g and a D,L-lactide:glycolide ratio of about 75:25, about 3% by weight cetyl alcohol, and about 2% by weight butylated hydroxyanisole, wherein the inherent viscosities of the first, second, and third polymers correspond to those measured for a 0.1% solution of the polymer in chloroform at 25° C.

Example Embodiment 23

The biodegradable intraocular implant of any one of the preceding example embodiments, comprising about 15% by weight of Compound 1:

Compound 1 about 5% by weight of a first polymer that is poly(D,L-lactide) having an acid end group and an inherent viscosity of about 0.16-0.24 dl/g, about 30% by weight of a second polymer that is poly(D,L-lactide) having an ester end group and an inherent viscosity of about 0.25-0.35 dl/g, about 45% by weight of a third polymer that is poly(D,L-lactide-co-glycolide) having an ester end group and an inherent viscosity of about 0.16-0.24 dl/g and a D,L-lactide:glycolide ratio of about 75:25, about 3% by weight cetyl alcohol, and about 2% by weight butylated hydroxyanisole, wherein the inherent viscosities of the first, second, and third polymers correspond to those measured for a 0.1% solution of the polymer in chloroform at 25° C.

Example Embodiment 24

The biodegradable intraocular implant of any one of the preceding example embodiments, comprising about 11% by weight of Compound 1:

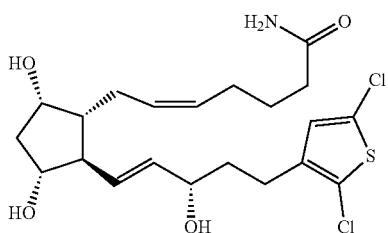

Compound 1 about 14% by weight of a first polymer that is poly(D,L-lactide) having an acid end group and an inherent viscosity of about 0.16-0.24 dl/g, about 35% by weight of a second polymer that is poly(D,L-lactide) having an ester end group and an inherent viscosity of about 0.25-0.35 dl/g, about 35% by weight of a third polymer that is poly(D,L-lactide-co-glycolide) having an ester end group and an inherent viscosity of about 0.16-0.24 dl/g and a D,L-lactide:glycolide ratio of about 75:25, about 3% by weight cetyl alcohol, and about 2% by weight butylated hydroxyanisole, wherein the inherent viscosities of the first, second, and third polymers correspond to those measured for a 0.1% solution of the polymer in chloroform at 25° C.

Example Embodiment 25

The biodegradable intraocular implant of any one of the preceding example embodiments, comprising about 11% by weight of Compound 1:

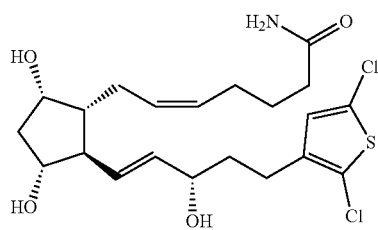

Compound 1 about 12% by weight of a first polymer that is poly(D,L-lactide) having an acid end group and an inherent viscosity of about 0.16-0.24 dl/g, about 30% by weight of a second polymer that is poly(D,L-lactide) having an ester end group and an inherent viscosity of about 0.25-0.35 dl/g, about 40% by weight of a third polymer that is poly(D,L-lactide-co-glycolide) having an ester end group and an inherent viscosity of about 0.16-0.24 dl/g and a D,L-lactide:glycolide ratio of about 75:25, about 5% by weight cetyl alcohol, and about 2% by weight butylated hydroxyanisole, wherein the inherent viscosities of the first, second, and third polymers correspond to those measured for a 0.1% solution of the polymer in chloroform at 25° C.

Example Embodiment 26

The biodegradable intraocular implant of any one of example embodiments 20 to 25, wherein the implant releases in vitro less than 30% of Compound 1 during the first 24 hours.

Example Embodiment 27

The biodegradable intraocular implant of example embodiment 26, wherein the implant releases in vitro less than 25% of Compound 1 during the first 24 hours.

Example Embodiment 28

The biodegradable intraocular implant of example embodiment 26, wherein the implant releases in vitro less than 20% of Compound 1 during the first 24 hours.

Example Embodiment 29

The biodegradable intraocular implant of example embodiment 26, wherein the implant releases in vitro less than 15% of Compound 1 during the first 24 hours.

Example Embodiment 30

The biodegradable intraocular implant of any one of example embodiments 7, 13 to 16, and 26 to 29, wherein the in vitro release of Compound 1 is measured in a phosphate buffered saline (PBS) solution at a pH of 7.4±0.05 and at 37° C., and wherein the PBS solution is a PBS solution that is free of magnesium and calcium and has a pH of 7.4±0.05 at 25° C.

Example Embodiment 31

The biodegradable intraocular implant of any one of the preceding example embodiments, wherein the implant is sized for placement in the anterior chamber of the eye.

Example Embodiment 32

The biodegradable intraocular implant of any one of the preceding example embodiments, wherein the diameter of the implant is about 150 μm and the implant contains about 5 μg or about 7.5 μg of Compound 1.

Example Embodiment 33

A method for reducing intraocular pressure in a patient, comprising placing a biodegradable intraocular implant of any of one of example embodiments 1 to 32 in an eye of the patient.

Example Embodiment 34

The method of example embodiment 33, wherein the patient is suffering from, diagnosed with, or at risk of developing elevated intraocular pressure or glaucoma.

Example Embodiment 35

The method of example embodiment 33 or 34, wherein the intraocular implant is placed in the anterior chamber of the eye in the patient.

Example Embodiment 36

The method of any one of example embodiments 33 to 35, wherein the patient is a human.

Example Embodiment 37

The biodegradable intraocular implant of any one of example embodiments 1 to 32 for use in a method of reducing intraocular pressure in a patient, the method comprising placing the intraocular implant in an eye of the patient.

Example Embodiment 38

The biodegradable intraocular implant for use of example embodiment 37 wherein the patient is suffering from, diagnosed with, or at risk of developing elevated intraocular pressure or glaucoma.

Example Embodiment 39

The biodegradable intraocular implant for use of example embodiment 37 or 38, wherein the intraocular implant is placed in the anterior chamber of the eye in the patient.

Example Embodiment 40

The biodegradable intraocular implant for use of any one of example embodiments 37 to 39, wherein the patient is a human.

Example Embodiment 41

Use of the biodegradable intraocular implant of any one of example embodiments 1 to 32 in the manufacture of a medicament for reducing intraocular pressure in a patient.

Example Embodiment 42

The use of example embodiment 41, wherein the patient is suffering from, diagnosed with, or at risk of developing elevated intraocular pressure or glaucoma.

Example Embodiment 43

The use of example embodiment 41 or 42, wherein the biodegradable intraocular implant, when administered to the patient, is placed in the anterior chamber of the eye in the patient.

Example Embodiment 44

The use of any one of example embodiments 41 to 43, wherein the patient is a human.

Example Embodiment 45

Use of the biodegradable intraocular implant of any one of example embodiments 1 to 32 in a method for reducing intraocular pressure in a patient, the method comprising placing the intraocular implant in an eye of the patient.

Example Embodiment 46

The use of example embodiment 45, wherein the patient is suffering from, diagnosed with, or at risk of developing elevated intraocular pressure or glaucoma.

Example Embodiment 47

The use of example embodiment 45 or 46, wherein the biodegradable intraocular implant is placed in the anterior chamber of the eye in the patient.

Example Embodiment 48

The use of any one of example embodiments 45 to 47, wherein the patient is a human.

Example Embodiment 49

A biodegradable intraocular implant substantially as described herein.

Example Embodiment 50

A biodegradable intraocular implant comprising Compound 1:

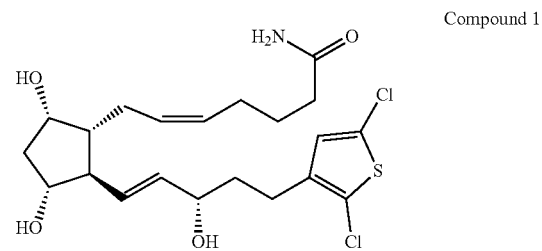 [SMILES: NC(=O)CCC/C=C\C[C@@H]1[C@@H](/C=C/[C@@H](O)CCc2cc(Cl)sc2Cl)[C@H](O)C[C@@H]1O]

Compound 1 substantially as described herein.

BRIEF DESCRIPTION OF THE DRAWINGS

FIG. 7 shows swelling study results for Implants 1 and 5 by image.

DETAILED DESCRIPTION

Definitions

Figure 1:
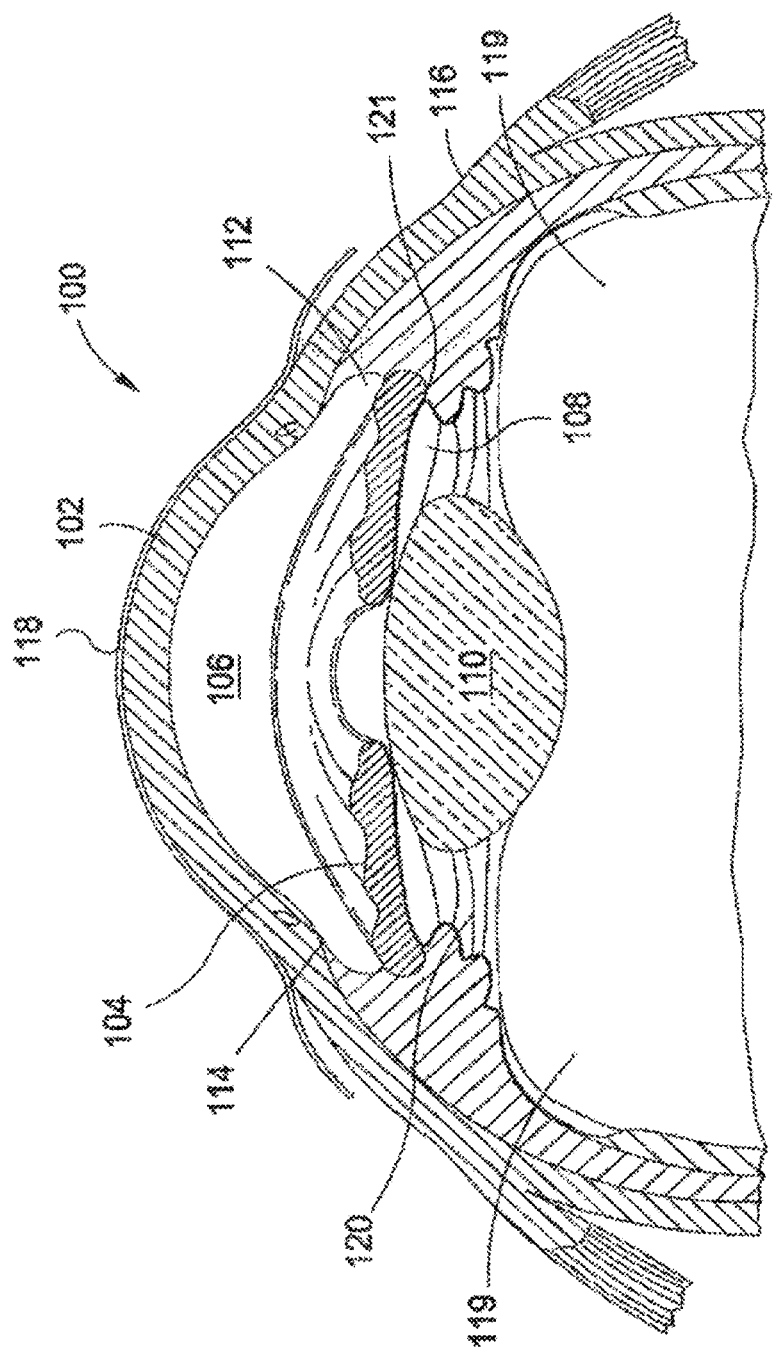
FIG. 1 shows a cross-section of the mammalian eye.

"Cumulative release profile" refers to the cumulative total percent of Compound 1 released from an implant into an ocular region in vivo over time or into a specific release medium (e.g., PBS) in vitro over time.

A "prodrug" means a compound (e.g., a drug precursor) that is transformed in vivo to yield an active form of the compound. The transformation can occur by various mechanisms (e.g., by metabolic or chemical processes), such as, for example, through hydrolysis.

An "intraocular implant" refers to a device or element that is configured to be placed in the eye. Examples include extruded filaments, comprising a biodegradable polymer material and a pharmaceutically active agent, such as Compound 1 associated with the polymer material, and cut to a length suitable for placement in an eye. Intraocular implants are generally biocompatible with the physiological conditions of an eye and do not cause adverse reactions in the eye. In certain embodiments described herein, an intraocular implant can be sized and formulated for placement in the anterior chamber or vitreous body of the eye. Intraocular implants can be placed in an eye without significantly disrupting vision of the eye. Intraocular implants comprising one or more biodegradable polymers and Compound 1 or a pharmaceutically acceptable salt thereof are examples of an intraocular implant (drug delivery system) within the scope of the present disclosure.

An "intracameral" implant is an intraocular implant that is sized and formulated for placement in the anterior chamber of the eye. Non-limiting examples include Implants 2-6 described in Table 2.

An "intravitreal" implant is an intraocular implant that is sized and formulated for placement in the vitreous body of the eye.

"Suitable for or configured for, sized for, or structured for insertion, implantation, or placement in (or into) an ocular region or site" with regard to an implant, means an implant which has a size (e.g., dimensions and weight) such that it can be inserted, implanted, or placed in an ocular region such as the anterior chamber or vitreous body of the eye without causing excessive tissue damage or significantly impairing the existing vision of the patient into which the implant is implanted or inserted.

"Treating" and "treatment" as used herein includes any beneficial effect in the eye of a patient produced by the present methods. Treatment of an ocular condition, such as ocular hypertension or elevated intraocular pressure, or glaucoma, can reduce or resolve the ocular condition or can reduce or retard the progression of one or more signs, symptoms, or risk factors of or associated with the ocular condition. The sign(s) or symptom(s) positively affected by the treatment will depend on the particular condition. Examples of beneficial (and therefore positive) effects produced by the present methods can include a reduction in intraocular pressure, ocular pain (i.e., eye pain), ocular swelling, and/or ocular inflammation. Treatment by any of the methods described herein using one or more of the intraocular implants described herein can, in some instances, also improve the general wellbeing, comfort, and/or visual performance of the eye.

"Active agent," "drug," "therapeutic agent," "therapeutically active agent," and "pharmaceutically active agent" refer to Compound 1.

A "patient" can be a human or non-human mammal in need of treatment.

The "eye" is the sense organ for sight, and includes the eyeball, or globe, the orbital sense organ that receives light and transmits visual information to the central nervous system. Broadly speaking the eye includes the eyeball and the ocular regions, tissues, and fluids which constitute the eyeball, the periocular muscles (such as the oblique and rectus muscles) and the portion of the optic nerve which is within or adjacent to the eyeball.

The term "therapeutically effective amount" or "effective amount" refers to the level or amount of active agent needed to treat an ocular condition, generally without causing significant negative or adverse side effects to the eye or a region of the eye to which the agent is administered.

The term "biodegradable polymer" refers to a polymer or polymers which degrade in vivo, and wherein degradation of the polymer or polymers over time occurs concurrent with or subsequent to release of the therapeutic agent. A biodegradable polymer can be a homopolymer, a copolymer, or a polymer comprising more than two different structural repeating units.

The term "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of an ocular region in an eye include the anterior chamber, the posterior chamber, the vitreous cavity (vitreous body or the vitreous), the choroid, the suprachoroidal space, the conjunctiva, the subconjunctival space, the sub-Tenon space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

Unless indicated otherwise herein, the term "about" when used in reference to a value (e.g., weight percentages) is intended to include values proximate to the recited value (and/or range of values) that are equivalent (e.g., bioequivalent) in terms of the functionality of the individual ingredient (e.g., active ingredient or excipient), the composition, or the embodiment. Furthermore, as will be understood by a skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements and that some values and amounts can be rounded up or down such that they would be "about the same" as another value or amount.

An anterior ocular condition is a disease, ailment or condition which affects or which involves an anterior ocular region or site (i.e. front of the eye), such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site. Glaucoma can be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site (i.e., back of the eye) such as choroid or sclera (in a position posterior to a plane through the posterior wall of the lens capsule), vitreous, vitreous chamber, retina, optic nerve (i.e., the optic disc), and blood vessels and nerves which vascularize or innervate a posterior ocular region or site. Glaucoma can also be considered a posterior ocular condition because the therapeutic goal is to prevent the loss of or reduce the occurrence of loss of vision due to damage to or loss of retinal cells or optic nerve cells (i.e., neuroprotection).

Size and Configuration of the Biodegradable Intraocular Implant

Biodegradable implants that are sized and formulated for placement in the eye of a patient (intraocular implants) and that comprise Compound 1, dispersed in a biodegradable polymer material (or matrix) can be useful for reducing intraocular pressure and treating glaucoma. Compound 1 is particularly effective for reducing intraocular pressure in an eye when administered directly into the anterior chamber of the eye. Biodegradable implants can be a safe, non-toxic, and effective means by which to administer this compound to the anterior chamber.

Consistent with this site of delivery, implants described herein can be sized and formulated to be received in the anterior chamber of the eye (e.g., a human eye), and in particular within the anterior chamber angle of the eye, with little or no adverse effects on the eye, particularly the corneal endothelium, and without obstructing or significantly impairing the vision of the patient. Patients receiving the implant will receive a therapeutically effective amount of Compound 1 and will ideally experience little or no hyperemia or inflammation in the eye following placement of the implant in the eye. In this regard, then, disclosed herein are intraocular implants that are sized and formulated for placement in the anterior chamber of the eye, that are biocompatible with the eye, causing little or no immunological reaction or inflammation in the eye, and that can be effective for reducing intraocular pressure in an eye for an extended period of time. The exceptional potency of Compound 1 for lowering IOP, for example, makes it possible to reduce the size of the intraocular implant needed to deliver a therapeutically effective dose of the IOP-lowering agent to target tissues and sites in the eye such as the anterior chamber, possibly minimizing potential irritation or injury to the tissues in the eye and more generally providing increased safety and greater overall benefit and comfort for the patient. Moreover, the use of smaller implants can reduce the time needed to completely degrade the implant in the eye following drug release. Furthermore, the ability to load the implants with larger amounts of Compound 1 (e.g., 15 wt % as opposed to lower amounts like 8 wt % or less) without having an initial burst release of compound 1 seen in other implants with Compound 1 can also result in the more beneficial smaller implants.

An implant can have a size suitable for insertion, placement or implantation in an ocular region or site, such as the anterior chamber, posterior chamber, or vitreous body of the eye. The size of an implant can affect the rate of release, period of treatment, and concentration of Compound 1 in treated tissue. At equal active agent loads, larger implants can deliver a proportionately larger dose.

An implant sized for placement in the anterior chamber (an intracameral implant) can generally have a diameter (or other dimension as appropriate for non-cylindrical filaments) of from about 100 to about 400 µm and a length of from about 0.5 to about 6 mm. The implants can generally be formed by a single or double extrusion process, can be cylindrical or non-cylindrical, and can have a total weight ranging from about 10 µg to about 500 µg. The weight can depend, in part, on the dosage desired. In some embodiments, implants suitable for placement in the anterior chamber of an eye and suitable for use according to the present disclosure can have a diameter of between about 100 µm and about 300 µm, a length of between about 0.5 mm and about 3 mm (e.g. about 2 mm), and a total weight of between about 10 µg and about 200 µg or between about 10 µg and about 100 µg. In some instances, the intracameral implant for reducing IOP has a total weight of from about 10 µg to about 100 µg, or more specifically from about 30 to about 100 µg, with doses of active compound (e.g., Compound 1) depending on the weigh percentage of active compound as described herein (e.g., with a weight percentage of about 15% of Compound 1, an approximately 33.3 µg implant would contain an approximately 5 µg amount of Compound 1 and an approximately 50 µg implant would contain an approximately 7.5 µg amount of Compound 1). One embodiment is an extruded biodegradable intraocular implant that is suitable for placement in the anterior chamber of an eye and that is about 200 µm or about 150 µm in diameter and about 1.5 mm or about 2 mm in length.

The eye(s) in some patients suffering from glaucoma or more generally ocular hypertension may be more receptive to placement of the biodegradable implant in the vitreous body of the eye. The vitreous body may accept larger implants of the same general formulation. For example, an intravitreal implant can have a length of about 1 mm to about 10 mm, a diameter of about 0.5 mm to about 1.5 mm, and a total weight of about 50 µg to about 5000 µg. The implant can be scaled up or down depending on the site of administration in the eye and the size or the vitreous volume of the patient. While in most cases a single implant can be found to reduce intraocular pressure in an eye for a sustained period, in some instances, the practitioner may find it useful to place two or more of the presently described implants in an ocular region of the eye to improve the therapeutic effect.

Regarding configuration, intraocular implants can be in the form of extruded rods or in the form of non-cylindrical filaments, having the dimensions described above. Wafers, sheets, or films and in some cases compressed tablets can also find use according to the present disclosure.

Biodegradable Polymer Material and Other Implant Components

In general, an implant according to the present disclosure will comprise or consist of a biodegradable polymer material and Compound 1 or a pharmaceutically acceptable salt thereof. The polymer material can comprise, consist of, or consist essentially of one, two, three, or more biodegradable polymers, and optionally one or more excipients to further improve the stability and/or release characteristics of the implant.

Examples of useful biodegradable polymers include polylactide (lactic acid) and polyglycolide (glycolic acid) polymers and copolymers thereof (e.g. poly(lactide-co-glycolide) copolymers). In some embodiments, the biodegradable polymer material can comprise a polylactide, a poly(lactide-co-glycolide), a mixture of two or more polylactide polymers (e.g., first and second polylactide polymers), a mixture of two or more poly(lactide-co-glycolide) copolymers, or a mixture of polylactide and poly (lactide-co-glycolide) polymers In particular forms of any of these implants, the polylactide polymer can be a poly(D,L-lactide) and the poly(lactide-co-glycolide) copolymer can be a poly(D,L-lactide-co-glycolide). In any of the aforementioned combinations, the two or more polymers can differ, one from the other, on the basis of their end group (e.g. acid and ester end groups), repeating unit, inherent viscosity, or any combination thereof. Polylactide and poly(lactide-co-glycolide) polymers used in the present implants can have either a carboxyl (—COOH) or ester end group. In addition, two or more poly(lactide-co-glycolide) polymers can differ one from the other by the lactide:glycolide ratio in each polymer, which can vary from about 85:15 to about 50:50 to about 75:25, depending on the polymer.

Poly(D,L-lactide), or PLA, can be identified by CAS Number 26680-10-4 and can be represented as:

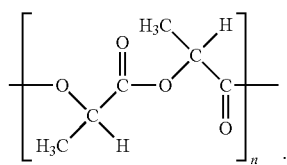

Poly(D,L-lactide-co-glycolide), or PLGA, can be identified by CAS Number 26780-50-7 and can be represented as:

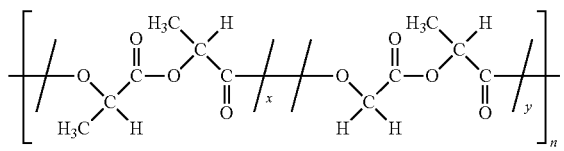

wherein x is the number of D,L-lactide repeat units and y is the number of glycolide repeat units, and n is the number of D,L-lactide-co-glycolide repeat units. Thus, poly(D,L-lactide-co-glycolide) (PLGA) comprises one or more blocks of D,L-lactide repeat units and one or more blocks of glycolide repeat units, where the size and number of the respective blocks can vary.

The molar percent of each monomer or repeat unit in a PLGA copolymer can be 0-100%, about 15-85%, about 25-75%, or about 35-65%. In some embodiments, the D,L-lactide can be about 50% to about 75%, about 48% to about 52%, or about 50%; about 73% to about 77%, or about 75% of the PLGA polymer on a molar basis. The balance of the polymer can essentially be glycolide repeat units. For example, glycolide can be about 25% to about 50%, about 23% to about 27%, or about 25%; about 48% to about 52%, or about 50% of the PLGA polymer on a molar basis. Other groups, such as terminal or capping groups (end group) can be present in small amounts. As described above, in some embodiments, PLGA copolymers are used in conjunction with PLA polymers. In some implants, a 75/25 PLGA polymer having an ester end group is used.

The hydrophilic or hydrophobic character of the end groups can be useful in varying polymer material degradation. Polymers with a hydrophilic end group can degrade faster than polymers with a hydrophobic end group because a hydrophilic group can take up water. Examples of suitable hydrophilic end groups include, but are not limited to, carboxyl (acid end group), hydroxyl, and polyethylene glycol. These groups can be introduced by using an appropriate initiator. End groups can also be introduced after polymerization is complete to convert the terminal hydroxyl groups into other end groups. For example, ethylene oxide can convert hydroxyl to polyethylene glycol. Hydrophobic ended (also referred to as capped or end-capped) polymers have an ester linkage hydrophobic in nature at the polymer terminus.

Other polymers of interest include or can be selected from hydroxyaliphatic carboxylic acids, either homopolymers or copolymers, hyaluronic acid, sodium hyaluronate, polycaprolactones, polysaccharides, polyethers, calcium alginate, celluloses, carboxymethyl cellulose, polyvinyl alcohol, polyesters and combinations thereof.

Useful polysaccharides can include, without limitation, calcium alginate, and functionalized celluloses, such as carboxymethylcellulose esters characterized by being water insoluble, and having a molecular weight of about 5 kD to about 500 kD, for example.

Release of a drug from a biodegradable polymer material is the consequence of several mechanisms or combinations of mechanisms. Some of these mechanisms include desorption from the implant's surface, dissolution, diffusion through porous channels of the hydrated polymer and erosion of the polymer(s) that make up the matrix. Erosion can be bulk or surface or a combination of both. The polymer matrix can release the therapeutic agent at a rate effective to sustain release of an amount of the agent (for example, Compound 1) for more than one month, for 2-3 months, for 3-6 months, or for 6 months or more after implantation into an eye. For example, an implant can comprise Compound 1, and the polymer material (or matrix) of the implant can degrade at a rate effective to sustain release of a therapeutically effective amount of Compound 1 for greater than one month, such as two, three, four, five, or six month(s) in vitro or after being placed in an eye, or, more specifically, after being placed in the anterior chamber the eye.

The one or more biodegradable polymers used to form the matrix (polymer material of the implant) are desirably subject to enzymatic or hydrolytic instability. Additional characteristics of the polymer(s) include biocompatibility, compatibility with the therapeutic component, ease of use of the polymer in making the implant of the present disclosure, a half-life in the physiological environment of at least about 6 hours, e.g. greater than about one day, and water insolubility.

A biodegradable polymer material degrades in vivo in a manner that provides for release of a therapeutically effective amount of the therapeutic agent for a period that is significantly greater than the in vivo life of the agent when administered in an eye drop formulation. As previously discussed, a polymer material can be a single polymer or copolymer, or, in some instances, a combination or blend of biodegradable polymers and/or copolymers.

In addition to the biodegradable polymer(s) and Compound 1 or a pharmaceutically acceptable salt thereof, an intraocular implant according to this disclosure can comprise one or more excipients to improve the stability (e.g., shelf life) of the therapeutic agent in the final implant, the ease of manufacture and handling of the implant, and/or the release characteristics of the implant. Compound 1, for example, is susceptible to oxidative degradation under various manufacturing, formulation, and storage conditions. The main degradation product is believed by the inventors to be the C-15 ketone.

Examples of excipients for any of these purposes can include preservatives, antioxidants, chelating agents, electrolytes, or other excipients. In general, the excipient, when present, can constitute 0.001 to 10% or up to 15% by weight of the implant, and can be selected from any of those named below.

Useful water soluble preservatives can include sodium bisulfite, sodium bisulfate, sodium thiosulfate, benzalkonium chloride, chlorobutanol, thimerosal, phenylmercuric acetate, phenylmercuric nitrate, methylparaben, benzyl alcohol, polyvinyl alcohol and phenylethyl alcohol.

Suitable electrolytes can include sodium chloride, potassium chloride, and the like, including $MgCl_2$. Zinc salts can also be of interest.

Examples of antioxidants include ascorbate, ascorbic acid, L-ascorbic acid, melatonin, butylated hydroxyanisole (BHA), butylated hydroxytoluene (BHT), thiols, polyphenols, tocopherols such as alpha-tocopherol, mannitol, reduced glutathione, various carotenoids, cysteine, taurine, tyrosine, superoxide dismutase, lutein, zeaxanthin, cryptoxanthin, astaxanthin, lycopene, N-acetylcysteine, carnosine, gamma-glutamylcysteine, quercitin, lactoferrin, vitamin E or an ester of vitamin E, retinyl palmitate, and derivatives thereof.

Useful chelating agents can be selected from, for example, ethylenediaminetetraacetic acid (EDTA), ethylenediamine, porphine, and vitamin B-12.

Other excipients can include alcohols such as, for example, hexadecanol (also referred to as cetyl alcohol and hexadecan-1-ol, and sometimes denoted as C16-OH). In some embodiments, the implant can comprise a straight chain or branched alcohol that is greater than 10 carbons in length.

Implants described herein can include a combination of two or more of the above-named excipients.

Oxygen can be an important element in the degradation pathway of a therapeutic agent such as Compound 1. Other or additional means for extending the shelf life and preserving the potency of the implant once manufactured can comprise the step of storing the implant in an oxygen-depleted or oxygen-poor atmosphere such as in a sealed pouch (e.g., an aluminum pouch) comprising an oxygen absorber pack. Additional steps can include filling the pouch with nitrogen or argon gas or some other inert gas before sealing the pouch to further remove oxygen from the pouch.

One embodiment is an intraocular implant according to this disclosure comprising an antioxidant that retains at least about 85%, at least about 90% or greater than about 95%, or at least about 98% of its initial potency (or that loses no more than about 5% or no more than about 2% of its initial potency) after storage of the extruded implant for one month or for three months at 25° C. in a sealed pouch comprising an oxygen absorber and/or inert gas. The initial potency can be based on the actual or theoretical amount of the active agent Compound 1 on a weight to weight basis (w/w) present in the implant immediately after implant manufacture. In some embodiments, the implant can further be contained in a needle-tipped ocular implant delivery device in the pouch and the pouch can further contain a desiccant.

In one embodiment the biodegradable polymer material comprises, consists essentially of, or consists of first, second, and third biodegradable polymers. The first and second polymers can be poly(D,L-lactide) polymers that differ one from the other by their end group (ester or acid) and/or their inherent viscosity (as determined for a 0.1% solution in chloroform at 25° C.), and the third polymer can be a poly(D,L-lactide-co-glycolide). The implant can optionally further comprise hexadecanol and/or butylated hydroxyanisole (BHA).

In one embodiment, the first polymer is a poly(D,L-lactide) having an ester end group and an inherent viscosity of 0.25-0.35 dl/g (as measured for a 0.1% w/v solution in chloroform at 25° C.) (e.g., R203S); the second polymer is a poly(D,L-lactide) having an acid end group (i.e, a carboxyl end group) and an inherent viscosity of 0.25-0.35 dl/g (as measured for a 0.1% w/v solution in chloroform at 25° C.) (e.g., R203H); and the third polymer is a poly(D,L-lactide-co-glycolide) having an ester end group, an inherent viscosity of 0.16-0.24 dl/g (as measured for a 0.1% w/v solution in chloroform at 25° C.), and a D,L-lactide:glycolide ratio of about 75:25 (e.g., RG752S).

In some embodiments, the first, second, and third biodegradable polymers are independently selected from the group consisting of:

R202H, which is a poly(D,L-lactide) having an acid end group and an inherent viscosity of 0.16-0.24 dl/g, as measured for a 0.1% solution in chloroform at 25° C.;

R202S, which is a poly(D,L-lactide) having an ester end group and an inherent viscosity of 0.16-0.24 dl/g, as measured for a 0.1% solution in chloroform at 25° C.;

R203H, which is a poly(D,L-lactide) having an acid end group and an inherent viscosity of 0.25-0.35 dl/g, as measured for a 0.1% solution in chloroform at 25° C.;

R203 S, which is a poly(D,L-lactide) having an ester end group and an inherent viscosity of 0.25-0.35 dl/g, as measured for a 0.1% solution in chloroform at 25° C.; and RG752S, which is a poly(D,L-lactide-co-glycolide) having an ester end group and an inherent viscosity of 0.16-0.24 dl/g (as measured for a 0.1% solution in chloroform at 25° C.), and a D,L-lactide:glycolide molar ratio of about 75:25.

The R202H, R202S, R203H, R203S, and RG752S PLA and PLGA polymers mentioned above are from the RESOMER® polymer product line produced by Evonik Industries AG, Germany and available from chemical suppliers such as Sigma-Aldrich/Millipore Sigma and others identifiable to a skilled person upon a reading of the present disclosure.

In one embodiment, the first polymer is a poly(D,L-lactide) having an ester end group and an inherent viscosity of 0.25-0.35 dl/g, the second polymer is a poly(D,L-lactide) having an acid end group and an inherent viscosity of 0.16-0.24 dl/g, and the third polymer is a poly(D,L-lactide-co-glycolide) having an ester end group and an inherent viscosity of 0.16-0.24 dl/g and a D,L-lactide:glycolide ratio of about 75:25, where the inherent viscosity of each polymer or copolymer is measured for a 0.1% solution of the polymer or copolymer in chloroform at 25° C.

In one specific embodiment, the first polymer is R203S, the second polymer is R202H, and the third polymer is RG752S, and the implant further comprises the excipient hexadecan-1-ol and/or BHA. In specific forms, the implant comprises from 0.001% to 10% by weight of the hexadecan-1-ol.

In another embodiment, the biodegradable polymer material comprises, consists essentially of, or consists of first and second biodegradable polymers, wherein the first polymer is a poly(D,L-lactide) having an ester end group and an inherent viscosity of 0.25-0.35 dl/g (as measured for a 0.1% w/v solution in chloroform at 25° C.) (e.g., R203S) and the second polymer is a poly(D,L-lactide) having an acid end group (i.e. carboxyl) and an inherent viscosity of 0.25-0.35 dl/g (as measured for a 0.1% w/v solution in chloroform at 25° C.) (e.g. R203H).

In another embodiment, the biodegradable polymer material comprises, consists essentially of, or consists of a poly(D,L-lactide) having an acid end group (i.e, a carboxyl end group) and an inherent viscosity of 0.16-0.24 dl/g (as measured for a 0.1% w/v solution in chloroform at 25° C.) (e.g, R202H).

In another embodiment, the biodegradable polymer material comprises, consists essentially of, or consists of a poly(D,L-lactide) having an acid end group (i.e. carboxyl end group) and an inherent viscosity of 0.25-0.35 dl/g (as measured for a 0.1% w/v solution in chloroform at 25° C.) (e.g. R203H).

One embodiment is an extruded biodegradable intracameral implant comprising Compound 1, hexadecan-1-ol (hexadecanol), and a biodegradable polymer material, wherein the biodegradable polymer material comprises, consists essentially of, or consists of first, second and third polymers, wherein the first polymer is R203S, the second polymer is R202H, and the third polymer is RG752S. The implant can further comprise an antioxidant. Non-limiting examples include Implants 2-7, the formulations for which are set forth below in Table 2.

One embodiment is a biodegradable intraocular implant comprising a biodegradable polymer material, hexadecan-1-ol, BHA, and about 15% by weight of Compound 1:

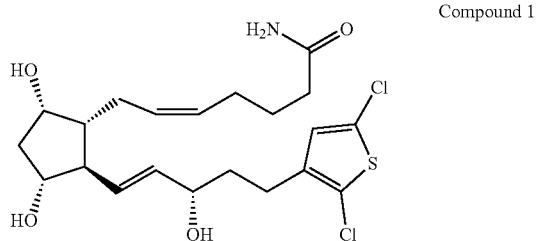

Compound 1 wherein the biodegradable polymer material comprises i) a poly(D,L-lactide) having an ester end group and an inherent viscosity of about 0.25-0.35 dl/g (e.g. R203S), ii) a poly(D,L-lactide) having an acid end group and an inherent viscosity of about 0.16-0.24 dl/g (e.g. R202H), and iii) a poly(D,L-lactide-co-glycolide) having an ester end group, an inherent viscosity of about 0.16-0.24 dl/g and a D,L-lactide:glycolide ratio of about 75:25 (e.g. R752S), wherein the inherent viscosity of each poly(D,L-lactide) and poly(D,L-lactide-co-glycolide) as given above is measured for a 0.1% solution of the polymer in chloroform at 25° C. In some embodiments the implant is an extruded implant.

In one embodiment the implant further comprises an antioxidant, a chelating agent, or both an antioxidant and a chelating agent. In specific forms the antioxidant is butylated hydroxyanisole or ascorbic acid and the chelating agent is EDTA. The intraocular implant can be sized for placement in the anterior chamber of the eye.

Implants according to any of the embodiments listed above can comprise greater than about 8% but no more than about 20% of Compound 1 by weight. For example, Compound 1 can be present in the implant in an amount of about 11, about 12, or about 15% by weight of the implant. An implant can contain about 15% by weight Compound 1.

One example embodiment is an intraocular implant comprising about 12% by weight of Compound 1, about 16% by weight of a first polymer that is poly(D,L-lactide) having an acid end group and an inherent viscosity of about 0.16-0.24 dl/g, about 25% by weight of a second polymer that is poly(D,L-lactide) having an ester end group and an inherent viscosity of about 0.25-0.35 dl/g, about 40% by weight of a third polymer that is poly(D,L-lactide-co-glycolide) having an ester end group and an inherent viscosity of about 0.16-0.24 dl/g and a D,L-lactide:glycolide ratio of about 75:25, about 5% by weight cetyl alcohol, and about 2% by weight butylated hydroxyanisole, wherein the inherent viscosities of the first, second, and third polymers correspond to those measured for a 0.1% solution of the polymer in chloroform at 25° C.

Another example embodiment is an implant comprising about 12% by weight of Compound 1, about 6% by weight of a first polymer that is poly(D,L-lactide) having an acid end group and an inherent viscosity of about 0.16-0.24 dl/g, about 30% by weight of a second polymer that is poly(D,L-lactide) having an ester end group and an inherent viscosity of about 0.25-0.35 dl/g, about 45% by weight of a third polymer that is poly(D,L-lactide-co-glycolide) having an ester end group and an inherent viscosity of about 0.16-0.24 dl/g and a D,L-lactide:glycolide ratio of about 75:25, about 5% by weight cetyl alcohol, and about 2% by weight butylated hydroxyanisole, wherein the inherent viscosities of the first, second, and third polymers correspond to those measured for a 0.1% solution of the polymer in chloroform at 25° C.

Another example embodiment is an implant comprising about 15% by weight of Compound 1, about 15% by weight of a first polymer that is poly(D,L-lactide) having an acid end group and an inherent viscosity of about 0.16-0.24 dl/g, about 25% by weight of a second polymer that is poly(D,L-lactide) having an ester end group and an inherent viscosity of about 0.25-0.35 dl/g, about 40% by weight of a third polymer that is poly(D,L-lactide-co-glycolide) having an ester end group and an inherent viscosity of about 0.16-0.24 dl/g and a D,L-lactide:glycolide ratio of about 75:25, about 3% by weight cetyl alcohol, and about 2% by weight butylated hydroxyanisole, wherein the inherent viscosities of the first, second, and third polymers correspond to those measured for a 0.1% solution of the polymer in chloroform at 25° C.

Another example embodiment is an implant comprising about 15% by weight of Compound 1, about 5% by weight of a first polymer that is poly(D,L-lactide) having an acid end group and an inherent viscosity of about 0.16-0.24 dl/g, about 30% by weight of a second polymer that is poly(D,L-lactide) having an ester end group and an inherent viscosity of about 0.25-0.35 dl/g, about 45% by weight of a third polymer that is poly(D,L-lactide-co-glycolide) having an ester end group and an inherent viscosity of about 0.16-0.24 dl/g and a D,L-lactide:glycolide ratio of about 75:25, about 3% by weight cetyl alcohol, and about 2% by weight butylated hydroxyanisole, wherein the inherent viscosities of the first, second, and third polymers correspond to those measured for a 0.1% solution of the polymer in chloroform at 25° C.

Another example embodiment is an implant comprising about 11% by weight of Compound 1, about 14% by weight of a first polymer that is poly(D,L-lactide) having an acid end group and an inherent viscosity of about 0.16-0.24 dl/g, about 35% by weight of a second polymer that is poly(D,L-lactide) having an ester end group and an inherent viscosity of about 0.25-0.35 dl/g, about 35% by weight of a third polymer that is poly(D,L-lactide-co-glycolide) having an ester end group and an inherent viscosity of about 0.16-0.24 dl/g and a D,L-lactide:glycolide ratio of about 75:25, about 3% by weight cetyl alcohol, and about 2% by weight butylated hydroxyanisole, wherein the inherent viscosities of the first, second, and third polymers correspond to those measured for a 0.1% solution of the polymer in chloroform at 25° C.

Another example embodiment is an implant comprising about 11% by weight of Compound 1, about 12% by weight of a first polymer that is poly(D,L-lactide) having an acid end group and an inherent viscosity of about 0.16-0.24 dl/g, about 30% by weight of a second polymer that is poly(D,L-lactide) having an ester end group and an inherent viscosity of about 0.25-0.35 dl/g, about 40% by weight of a third polymer that is poly(D,L-lactide-co-glycolide) having an ester end group and an inherent viscosity of about 0.16-0.24 dl/g and a D,L-lactide:glycolide ratio of about 75:25, about 5% by weight cetyl alcohol, and about 2% by weight butylated hydroxyanisole, wherein the inherent viscosities of the first, second, and third polymers correspond to those measured for a 0.1% solution of the polymer in chloroform at 25° C.

Therapeutic Agent

Compound 1 can be prepared by methods known in the art. For example, see U.S. Pat. Nos. 6,602,900, 6,124,344, 5,741,810, and 5,834,498.

The present disclosure includes biodegradable intraocular implants made by an extrusion process that can be effective for reducing intraocular pressure in an eye of a patient for an extended period of time. Generally, the implant comprises, consists essentially of, or consists of a biodegradable polymer material and a therapeutic agent comprising Compound 1 and the intraocular implant is suitable for placement in the anterior chamber of the eye. The intraocular implant can release from about 10 to about 50 ng of the therapeutic agent per day for at least one month in vitro.

In general, the therapeutic agent of the implant can constitute 1% to about 90% of the total weight of the implant. In some embodiments the therapeutic agent can represent from greater than 8% to 20% of the total weight of the implant. In some embodiments, the amount of Compound 1 in an implant on weight to weight basis (w/w) does not exceed 15% of the total weight of the implant. Accordingly, in implants comprising Compound 1, Compound 1 can constitute from greater than 8% to 15% of the implant by weight, and in particular forms constitutes 11, 12, or 15% of the implant by weight. The weight percentage of Compound 1 in an implant at these prescribed levels (e.g. 15%) can avoid undesirably rapid or burst-like release of the drug upon placement of the implant in a liquid environment such as the eye.

In an implant according to the present disclosure, Compound 1, can be dispersed or distributed in, and/or covering, and/or surrounded by a biodegradable polymer material. When the implant contacts physiological fluid, such as ocular fluid (e.g. aqueous humor), in vivo, the physiological fluid can contact the portion of Compound 1 that is on the surface of the implant, but may not have contact with the portion of the Compound that is dispersed inside the polymer material. Once implanted, the biodegradable polymer can begin to be hydrated. Hydration of an implant can improve diffusion and release of Compound 1. Additionally, the implant can begin to degrade or erode over time. Degradation can increase hydration, increase the mobility of the polymer chains, and create pores for faster diffusion. Thus, implants can be configured so that the Compound is released from the polymer material as the polymer material is hydrated and/or degrades in vivo. Since hydration decomposition and/or degradation of the implant can take a substantial amount of time—and can be significantly longer than the normal decay period of the Compound when administered by a normal eye drop formulation—an implant can provide sustained release. Sustained release can continue for as long as at least some of the biodegradable polymer material containing at least a portion of Compound 1 remains intact.

The rate at which Compound 1 is released from an implant and the duration for which an implant releases Compound 1 can depend upon a variety of factors including, but not limited to, implant size and shape, particle size of the Compound, the solubility of the Compound, the ratio of the Compound to polymer material, the polymer(s) used (including monomer ratios in the polymer used, polymer end groups, and polymer molecular weight), polymer crystallinity, the method of manufacture, the surface area exposed, polymer material erosion rate, and the biological environment the implants reside in post dosing, etc.

Implants comprising a biodegradable polymer material of the type described above can provide for a constant, steady release of Compound 1 for extended periods, such as greater than 1 month, such as 2, 3 months, 4-5 months, or for 6 months. In particular, it has been surprisingly found by the inventors that the implant formulations described herein provide a controlled release, with low burst, of Compound 1 with drug loadings of, for example, 15% (w/w).

In particular, the biodegradable intraocular implant comprises a biodegradable polymer material and Compound 1, wherein Compound 1 is in an amount between about 8 and about 20% (such as from about 9 to about 18%, from about 9 to about 17%, from about 9 to about 16%, from about 9 to about 15%, and from about 10 to about 15%) by weight of the implant and wherein the implant releases in vitro less than about 30% of its drug load on day 1 (e.g. first 24 hours after implantation), for example, less than about 1%, less than about 2%, less than about 3%, less than about 4%, less than about 5%, less than about 6%, less than about 7%, less than about 8%, less than about 9%, less than about 10%, less than about 11%, less than about 12%, less than about 13%, less than about 14%, less than about 15%, less than about 16%, less than about 17%, less than about 18%, less than about 19%, less than about 20%, less than about 21%, less than about 22%, less than about 23%, less than about 24%, less than about 25%, less than about 26%, less than about 27%, less than about 28%, less than about 29%, and ranges in between those amounts. An in vitro release of greater than about 30% of the drug load on day 1 would be considered to be a burst release.

Accordingly, in some embodiments, the in vitro release rate of the drug load on day 1 can be between about 1% and about 30%, between about 2% and about 30%, between about 3% and about 30%, between about 4% and about 30%, between about 5% and about 30%, between about 6% and about 30%, between about 7% and about 30%, between about 8% and about 30%, between about 9% and about 30%, between about 10% and about 30%, between about 11% and about 30%, between about 12% and about 30%, between about 13% and about 30%, between about 14% and about 30%, between about 15% and about 30%, between about 16% and about 30%, between about 17% and about 30%, between about 18% and about 30%, between about 19% and about 30%, between about 20% and about 30%, between about 21% and about 30%, between about 22% and about 30%, between about 23% and about 30%, between about 24% and about 30%, between about 25% and about 30%, between about 26% and about 30%, between about 27% and about 30%, between about 28% and about 30%, between about 29% and about 30%, and ranges in between.

In other embodiments, the in vitro release rate of the drug load on day 1 can be between about 1% and about 25%, between about 2% and about 25%, between about 3% and about 25%, between about 4% and about 25%, between about 5% and about 25%, between about 6% and about 25%, between about 7% and about 25%, between about 8% and about 25%, between about 9% and about 25%, between about 10% and about 25%, between about 11% and about 25%, between about 12% and about 25%, between about 13% and about 25%, between about 14% and about 25%, between about 15% and about 25%, between about 16% and about 25%, between about 17% and about 25%, between about 18% and about 25%, between about 19% and about 25%, between about 20% and about 25%, between about 21% and about 25%, between about 22% and about 25%, between about 23% and about 25%, between about 24% and about 25%, and ranges in between.

In other embodiments, the in vitro release rate of the drug load on day 1 can be between about 1% and about 20%, between about 2% and about 20%, between about 3% and about 20%, between about 4% and about 20%, between about 5% and about 20%, between about 6% and about 20%, between about 7% and about 20%, between about 8% and about 20%, between about 9% and about 20%, between about 10% and about 20%, between about 11% and about 20%, between about 12% and about 20%, between about 13% and about 20%, between about 14% and about 20%, between about 15% and about 20%, between about 16% and about 20%, between about 17% and about 20%, between about 18% and about 20%, between about 19% and about 20%, and ranges in between.

In other embodiments, the in vitro release rate of the drug load on day 1 can be between about 1% and about 15%, between about 2% and about 15%, between about 3% and about 15%, between about 4% and about 15%, between about 5% and about 15%, between about 6% and about 15%, between about 7% and about 15%, between about 8% and about 15%, between about 9% and about 15%, between about 10% and about 15%, between about 11% and about 15%, between about 12% and about 15%, between about 13% and about 15%, between about 14% and about 15%, and ranges in between.

U.S. Pat. No. 9,889,142 (the '142 patent) describes extended, long term reduction of intraocular pressure in the eye which is provided by intraocular administration of one or more of the biodegradable intraocular implants comprising Compound 1. However, the '142 patent describes that, compared to an implant comprising Compound 1 in an amount of less than or equal to 8.0 wt %, an implant comprising the therapeutic agent in an amount of greater than 8.0 wt %, with the biodegradable polymer amounts described in the '142 patent, showed a significant initial burst of release of Compound 1 and/or provided very fast release rates (e.g. about 55% release on day 1 for an implant having 12% drug loading) that were generally considered to be unsuitable for the intended therapeutic uses. Such an initial burst release was surprisingly not seen with the implant formulations described herein even at drug loadings of over 8 wt % (e.g. 15 wt %).

The in vitro release rate of Compound 1 from the implant can be measured by following a USP approved method for dissolution or release test (USP 23; NF 18 (1995) pp. 1790-1798). For example, using the infinite sink method, a weighed sample of an implant is added to a measured volume of a solution (release medium) containing 0.9% NaCl (aq) or phosphate buffered saline, where the solution volume will be such that the therapeutically active agent concentration after release is less than 20%, and in some embodiments less than 5%, of saturation. The mixture is maintained at 37° C. and stirred or shaken slowly to ensure diffusion of therapeutically active agent from the implant. The appearance of the therapeutically active agent in the solution or release medium as a function of time can be followed by various methods known in the art, such as spectrophotometry, HPLC, mass spectrometry, etc.

In particular, in some embodiments, the in vitro release rate of compound 1 is measured in a phosphate buffered saline (PBS) solution at a pH of 7.4±0.05 and at 37° C., wherein the PBS solution is a PBS solution that is free of magnesium and calcium and has a pH of 7.4±0.05 at 25° C. As would be apparent to a skilled person, phosphate buffered saline (PBS) is a buffered saline solution containing disodium hydrogen phosphate, sodium chloride, potassium chloride, and potassium dihydrogen phosphate. PBS can also be prepared to contain calcium chloride and magnesium chloride in addition to the aforementioned sodium chloride and potassium chloride, or it can be prepared without calcium chloride and magnesium chloride (i.e. be free of magnesium and calcium). PBS is a buffer that can simulate approximate physiological pH of about 7.4 (e.g. 7.4±0.05) as well as simulate the approximate osmolarity and ion concentrations of many physiological fluids, including those in the eye. Accordingly, the PBS used to measure the in vitro release rate of compound 1 is PBS containing disodium hydrogen phosphate, sodium chloride, potassium chloride, and potassium dihydrogen phosphate that is free of magnesium and calcium and has a pH of 7.4±0.05 at 25° C., and can be prepared according to known recipes such as the Cold Spring Harbor recipe (see, e.g., www web page cshprotocols.cshlp.org/content/2006/1/pdb.rec8247), or it can be purchased as a powder (or other solid mixture of the non-water ingredients) that can be reconstituted in water according to the manufacturer's instructions (see, e.g., Sigma-Aldrich/Millipore-Sigma catalog number P5368).

The in vitro release rate of compound can be measured by incubating an implant in about 1 mL to about 3 mL of the aforementioned PBS at pH 7.4 in a glass scintillation vial at 37° C. under mild agitation (50 rpm). At designated time points, the release medium can be completely removed and replaced with fresh PBS. The amount of drug in the recovered release medium can be analyzed by, for example, HPLC, in triplicate if desired.

An intraocular implant according to the present disclosure can release about 5 to about 100 nanograms, about 5 to about 200 nanograms of Compound 1 per day, about 10 to about 200 nanograms of Compound 1 per day, about 5 to about 100 nanograms of Compound 1 per day, about 10 to about 100 nanograms of Compound 1 per day, about 10 to about 50 nanograms of Compound 1 per day, at least about 10 ng but not more than about 50 ng of Compound 1 per day, from about 10 to about 35 ng of Compound 1 per day, or from about 20 to about 35 nanograms of Compound 1 per day for greater than about 1 month, greater than about 2 months, between about 1 and about 3 months, for about 3 to about 6 months, or for about 6 to about 12 months or more.

Specific embodiments include, but are not limited to, an extruded intraocular implant sized for placement in the anterior chamber of the eye and comprising any one of the formulations given for Implant Nos. 2 to 7 in Table 2.

Methods of Manufacture

Various techniques can be employed to make the intraocular implants described herein. Useful techniques can include extrusion methods (for example, hot melt extrusion) to produce rod-shaped implants (or fibers), compression methods to produce tablets, wafers, or pellets, and solvent casting methods to produce biodegradable sheets, films, and dry powders. Emulsion methods to produce a plurality of microspheres can also be of use in preparing a biodegradable intraocular drug delivery system for the sustained release of Compound 1 into an eye in a patient. Accordingly, one embodiment provides for a pharmaceutical composition suitable for placement in an ocular region of an eye and comprising a plurality of biodegradable microspheres encapsulating Compound 1 or a pharmaceutically acceptable salt thereof.

An extruded implant can be made by a single or double extrusion method, and can be made with a piston or twin screw extruder, for example. Choice of technique, and manipulation of technique parameters employed to produce the implants can influence the release rates of the drug. Extrusion methods can allow for large-scale manufacture of implants and result in implants with a progressively more homogenous dispersion of the drug within a continuous polymer matrix, as the production temperature is increased. Extrusion methods can use temperatures of from about 50° C. to about 150° C., or from about 70° C. to about 100° C., or lower as necessary.

In one embodiment, an intraocular implant according to the present disclosure is produced by an extrusion process. Polymers and excipients, if any, are generally blended with the therapeutic agent and then co-extruded at a selected temperature to form a filament comprising a biodegradable polymer matrix (or material) and the therapeutic agent dispersed within and/or distributed throughout the matrix (or material). If desired the filament can be pulverized and re-extruded to form a double extruded implant.

In one variation of producing implants by an extrusion process, the therapeutic agent, biodegradable polymer(s), and, optionally, one or more excipients are first mixed at room temperature (blended in a container) and then heated to a temperature range of 50° C. to 150° C., for a time period of between 1 and 60 minutes, such as 1 to 30 minutes, 5 minutes to 15 minutes, or 10 minutes. The mixture is then extruded through a nozzle at a temperature of 60° C. to 130° C., or at 80° C. The extruded filament is then cut to desired lengths to produce intraocular implants having a specific weight. The orifice of the nozzle through which the mixture is extruded will generally have a diameter appropriate to the desired diameter of the implant, but if necessary the extruded filament can be pulled from the nozzle to further reduce the diameter of the implant. The extruded implant can be generally cylindrical or non-cylindrical, having a length and diameter (or other dimension as appropriate to non-cylindrical fibers) suitable for placement in an ocular region of the eye such as the anterior chamber or vitreous body.

One possible method for producing an intraocular implant of the present disclosure uses a combination of solvent casting and hot melt extrusion. See, for example, US 2010/0278897. In this method, a dry powder or film is first prepared by dissolving all materials (active agent, polymer(s), and excipients, if any) in an appropriate solvent, such as ethyl acetate, to form a solution. The solution is then cast into a suitable container (e.g., a TEFLON® dish), and then dried in a vacuum oven overnight to form a dry film. The film is then ground into particles, which are collected and extruded by hot melt extrusion to prepare a filament containing the active agent and one or more biodegradable polymers. The filament can be cut to a length and thereby weight suitable for placement in the eye. The extrusion temperature for this process can range from 50° C. to 150° C.

Accordingly, the present disclosure encompasses methods for making and using extruded biodegradable implants (which can be generally referred to as extruded rods or fibers) suitable for placement in an eye of a patient to reduce intraocular pressure, including elevated intraocular pressure in the eye.

Modes and Sites of Administration and Methods of Treatment

To provide for the intended therapeutic effect (e.g., long term reduction of intraocular pressure) in a patient, including one suffering from glaucoma, an implant according to the present disclosure can be placed in the anterior chamber of the eye. The anterior chamber refers to the space inside the eye between the iris and the innermost corneal surface (endothelium). In some patients, however, it may be necessary to place the implant in the vitreous body of the eye. The posterior chamber refers to the space inside the eye between the back of the iris and the front face of the vitreous. The posterior chamber includes the space between the lens and the ciliary process, which produces the aqueous humor that nourishes the cornea, iris, and lens and maintains intraocular pressure. Referring to FIG. 1, these and other ocular regions of the eye (100) are shown in cross-section. Particular regions of the eye (100) include the cornea (102) and iris (104), which surround the anterior chamber (106). Behind the iris (104) is the posterior chamber (108) and lens (110). Within the anterior chamber is the anterior chamber angle (112) and trabecular meshwork (114). Also shown are the corneal epithelium (118), sclera (116), vitreous (119), ciliary zonules (120), and ciliary process (121). The posterior segment of the eye is the rear two-thirds of the eyeball (behind the lens), and includes the vitreous, the retina, and the optic nerve.

To reduce intraocular pressure and treat glaucoma in a patient, an implant described herein can be implanted into the anterior chamber (or other ocular region) of an eye of a mammal as monotherapy to deliver a therapeutic agent (such as Compound 1) into the anterior chamber of the eye without the need for eye drops. Alternatively, the implant can be used with eyedrops as an adjunctive therapy. In some embodiments, inserting an implant described herein into the anterior chamber of an eye can reduce intraocular pressure in the eye by at least about, for example, 20% or 30% or more as compared to the baseline IOP. The patient can be a human or non-human mammal suffering from elevated intraocular pressure or glaucoma and therefore in need of treatment. In some embodiments, the implant can release Compound 1 according to linear or pseudo zero order kinetics for at least one month after placement of the implant in an eye.

Biodegradable implants can be inserted into an eye by a variety of methods, including placement by forceps, by trocar, or by a hand-held needle-equipped (or needle-tipped) delivery device (applicator). Some hand held applicators can be used to insert one or more biodegradable implants into the eye. Hand-held applicators can comprise an 18-30 GA (gauge) stainless steel needle, a lever, an actuator, and a plunger or push rod to facilitate ejection of the implant. An implant can be inserted by a scleral, limbal, or corneal route to access the anterior chamber. Alternately, an implant can be inserted into the vitreous using an appropriate applicator with a needle or cannula of length suitable for accessing the target site and delivery of the implant. Some methods for inserting an implant include accessing the target area within the ocular region with a needle, trocar or implantation device. Once within the target area, e.g., the anterior chamber or the vitreous, a lever on a hand held device can be depressed to cause an actuator to drive a plunger or push rod forward. As the plunger moves forward, it can push the device or implant into the target area (such as the vitreous or the anterior chamber). One example of an ocular implant delivery device is disclosed in U.S. Patent Application Publication 2004/0054374. Another example can be found in U.S. Pat. No. 6,899,717.

Accordingly, methods for treating glaucoma and reducing intraocular pressure in an eye of a patient as discussed herein can comprise administering a biodegradable intraocular implant of the type presently disclosed to the eye by injection into the anterior chamber (intracameral injection) or vitreous body of the eye (intravitreal injection). A syringe apparatus including an appropriately sized needle (for example, a 22, 25, 27, 28, or 30 gauge needle) can be useful for injecting one or more implants into these regions in the eye. Accordingly, the width or diameter of the implant can be selected so as to allow the implant to be received in and translated through the lumen of the needle gauge selected.

Prior to use in a subject, an implant can be sterilized with a suitable dose of, for example, beta-radiation. Preferably, the sterilization method does not substantially reduce the therapeutic activity of the therapeutic agent in the implant or preserves at least 50 or 80% or more of the initial activity.

Daily dosages of Compound 1 in the range of about 5 to about 100 nanograms, about 5 to about 200, about 10 to about 100 nanograms, or even about 5 to about 50 nanograms, when delivered or released directly into the anterior chamber, can be a therapeutically effective amount for reducing intraocular pressure in an eye of a patient.

The patient is typically a human or non-human mammal that is experiencing or diagnosed with elevated intraocular pressure or ocular hypertension in one or both eyes. The patient can be further defined as one suffering from glaucoma, since glaucoma frequently includes elevated intraocular pressure. Accordingly, the implants described herein can be used generally to reduce elevated intraocular pressure in an eye and to treat glaucoma in a patient. In this regard, one embodiment is a method of reducing ocular hypertension or elevated intraocular pressure in a patient in need thereof, the method comprising placing a biodegradable intraocular implant according to the present disclosure in an eye of the patient.

Patients that can be effectively treated with a biodegradable intracameral implant comprising Compound 1 or a pharmaceutically acceptable salt thereof can include those having, suffering from, or diagnosed with glaucoma, open-angle glaucoma, closed-angle glaucoma, chronic angle-closure glaucoma, patent iridotomy, ocular hypertension, elevated intraocular pressure, pseudoexfoliative glaucoma, or pigmentary glaucoma. An implant according to this disclosure can be effective for reducing intraocular pressure in an eye that has low, normal, or elevated intraocular pressure. Therefore, an implant according to this disclosure can be effective for treating glaucoma in all its forms, including glaucoma characterized by elevated intraocular pressure, as well as low-tension or normal-tension glaucoma, since these patients, too, can potentially benefit from a further reduction in intraocular pressure. Because of their ability to release therapeutically effective amounts of a potent intraocular pressure-reducing agent, such as Compound 1, for sustained periods, implants of the instant disclosure are expected to be capable of reducing intraocular pressure in these patients for long periods without the need for frequent intraocular injections or regular instillation of eye drops to the ocular surface as can be necessary with topical therapy. Moreover, the greater potency of Compound 1 for lowering IOP relative to some other prostamides and anti-glaucoma agents makes it possible to produce smaller implants with longer administration periods that are safer and better for the eye and therefore the patient.

Thus, one embodiment of the present disclosure is a method for reducing intraocular pressure (IOP) in an eye, the method comprising placing a biodegradable intraocular implant as disclosed herein in the eye, wherein the implant reduces intraocular pressure in the eye for an extended period of time. The implant can be placed in an ocular region of the eye and can, therefore, be sized for placement in an ocular region of the eye. The patient may have low or normal intraocular pressure or may be suffering from elevated intraocular pressure, sometimes referred to as ocular hypertension, or the patient may have glaucoma. In a more specific form, the patient is suffering from or diagnosed with glaucoma or elevated intraocular pressure and the implant is placed in the anterior chamber or vitreous body of the affected eye(s). In a specific embodiment the implant is placed in the anterior chamber angle (or iridocorneal angle), and even more specifically in the inferior iridocorneal angle, of the affected eye(s). In any of these methods, the Compound in the implant (i.e., the therapeutic agent) can comprise, consist essentially of, or consist of Compound 1, a pharmaceutically acceptable salt of Compound 1, or any mixture thereof, and the implant can be placed in the anterior chamber or vitreous body of the eye via intracameral or intravitreal injection. In specific embodiments the implant is placed in the anterior chamber angle (or iridocorneal angle) of the eye. The implant can also be placed in the subconjunctival region of the eye.

Accordingly, the disclosure provides for a method of treating glaucoma in a patient, comprising the step of placing a biodegradable intraocular implant as described herein in an eye of the patient. The implant can be placed in the anterior chamber of the eye or other ocular region of the eye, to thereby treat the glaucoma.

Some embodiments include a method of administering Compound 1 without eye drops, the method comprising inserting an implant described herein into an eye of a patient in need thereof. The implant can be placed in the anterior chamber of the eye.

In particular forms of the treatment method, one or more intraocular implants comprising Compound 1 or a pharmaceutically acceptable salt thereof can be placed, or more specifically injected, into the anterior chamber of an eye to thereby reduce intraocular pressure and ocular hypertension in the eye. Accordingly, the intraocular implant can, for example, be sized and formulated for placement in the anterior chamber the eye. Such implants can be referred to as "intracameral" implants.

Implants of the present disclosure are designed to provide long lasting relief from elevated intraocular pressure (or ocular hypertension) by providing a sustained, continuous release of a therapeutically effective amount of Compound 1 or any pharmaceutically acceptable salt thereof directly into the affected region of the eye, such as the anterior chamber of the eye. In this context, a therapeutically effective amount of Compound 1 can be a dosage of between about 5 to about 100 ng/day, about 5 to about 200 ng/day, about 10 to about 200 ng per day, about 5 to about 50 ng/day, or more specifically about 10 to about 50 ng/day, or even more specifically about 15 ng/day, about 20 ng/day, about 30 ng/day, about 40 ng/day, or about 50 ng/day. The patient can be a human or non-human mammal in need of treatment for ocular hypertension (elevated intraocular pressure) or glaucoma. The implant can be in the form of an extruded filament or compressed tablet. Other forms can include wafers, films, or sheets. The extruded filament can be a cylindrical or non-cylindrical rod having a diameter and cut to a length suitable for placement in the eye, such as the anterior chamber or vitreous body of the eye.

EXAMPLES

The following examples are intended only to illustrate the methods of the present disclosure and should in no way be construed as limiting the methods of the present disclosure.

Example 1

Manufacture of Implants

Implants 1-6 in Table 2 were manufactured as follows. The drug substance, polymers, and additives were added to a stainless steel (SS) container containing two 10 mm SS balls. The powders were blended in a Turbula mixer for 15 min, hand mixed using a spatula, and then blended again in the Turbula mixer for an additional 15 min. The resulting powder blend was then processed into filaments using a twin-screw microcompounder/extruder. The extrusions were conducted at the process settings summarized in Table 1.

TABLE 1

Summary DSM extrusion condition for Compound 1 containing implant

| Implant No | Extrusion Temperature (° C.) | Screw Speed (rpm) |
|---|---|---|
| 1 | 70-80 | 40 |
| 2 | 70-90 | 40 |
| 3 | | |
| 4 | | |
| 5 | | |
| 6 | | |
| 7 | | |

The formulation composition and notebook references are summarized in Table 2.

TABLE 2

Summary of Compound 1 containing implant composition

| Implant | Composition (%, w/w) | | | | | |
|---|---|---|---|---|---|---|
| No | Drug | R203S | RG752S | R202H | C16-OH | BHA | EDTA |
| 1 | 8 | 50.3 | 22.4 | 11.2 | 5.6 | 2 | 0.5 |
| 2 | 12 | 25 | 40 | 16 | 5 | 2 | — |
| 3 | 12 | 30 | 45 | 6 | 5 | 2 | — |
| 4 | 15 | 25 | 40 | 15 | 3 | 2 | — |
| 5 | 15 | 30 | 45 | 5 | 3 | 2 | — |
| 6 | 11 | 35 | 35 | 14 | 3 | 2 | — |
| 7 | 11 | 30 | 40 | 12 | 5 | 2 | |

The extruded filaments were randomly selected and cut to produce implants of specific weights using an auto-cutter. A total of 50 implants were cut for each implant number. The target implant weight for 150-μm diameter filaments were 50±2.5 μg (5%). Implants were stored in a glass vial, sealed in a foiled pouch with a desiccant, and e-beam sterilized at 25±10% kGy before testing.

Example 2

In Vitro Drug Release Rate Assay

In vitro drug release studies were performed by placing each implant in 2 ml of aqueous incubation buffer (release medium) in a 10-ml glass vial. The vials were maintained in a shaking water bath at 37° C. and 50 rpm. This incubation buffer consisted of phosphate buffered saline (PBS) (137 mM NaCl, 2.7 mM KCl, and 10 mM phosphate buffer) at pH 7.4. At each designated time-point all 2 ml of the release medium in each vial was sampled and replaced with an equal volume of fresh release medium. Sink conditions in the release medium was maintained throughout the study.

Figure 2:
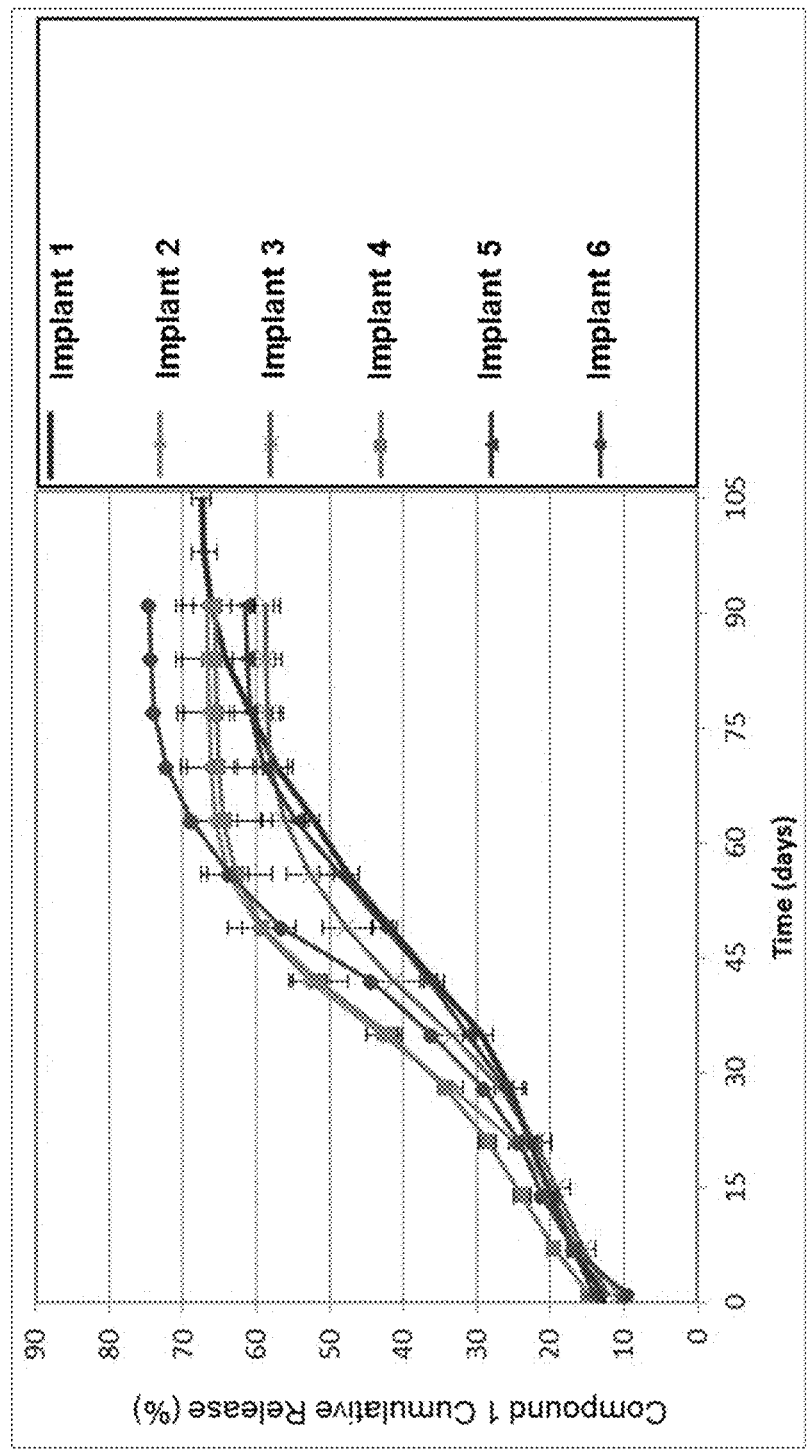
FIG. 2 shows the in vitro cumulative total percent release of Compound 1 into phosphate buffered saline (0.01 M; pH 7.4) at 37° C. over time for six (6) separate implants (Implants 1-6). The composition of each implant is described in Table 2.
Figure 3:
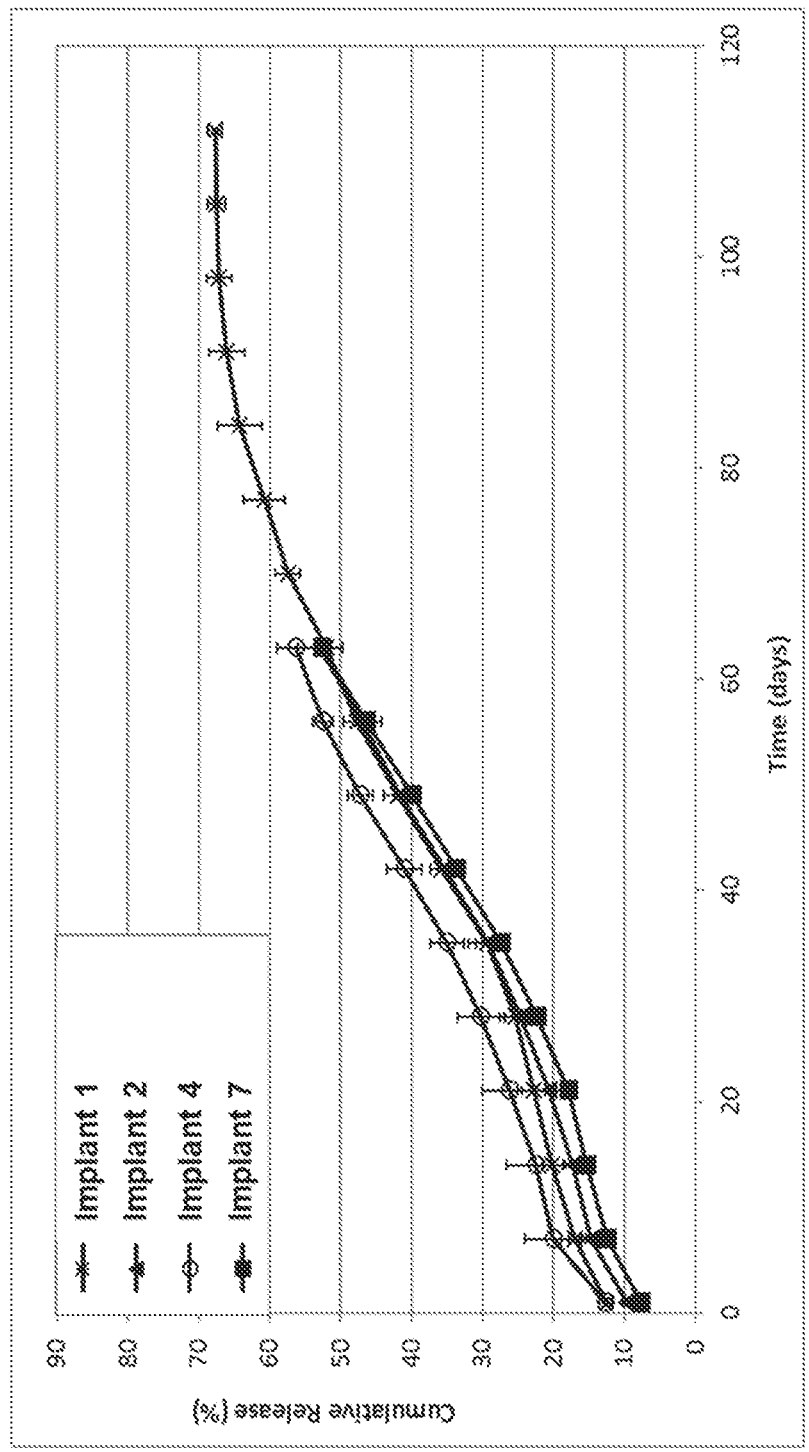
FIG. 3 shows the in vitro cumulative total percent release of Compound 1 into phosphate buffered saline (0.01 M; pH 7.4) at 37° C. over time for Implants 1, 2 4, and 7. The composition of each implant is set forth in Table 2.
Figure 4:
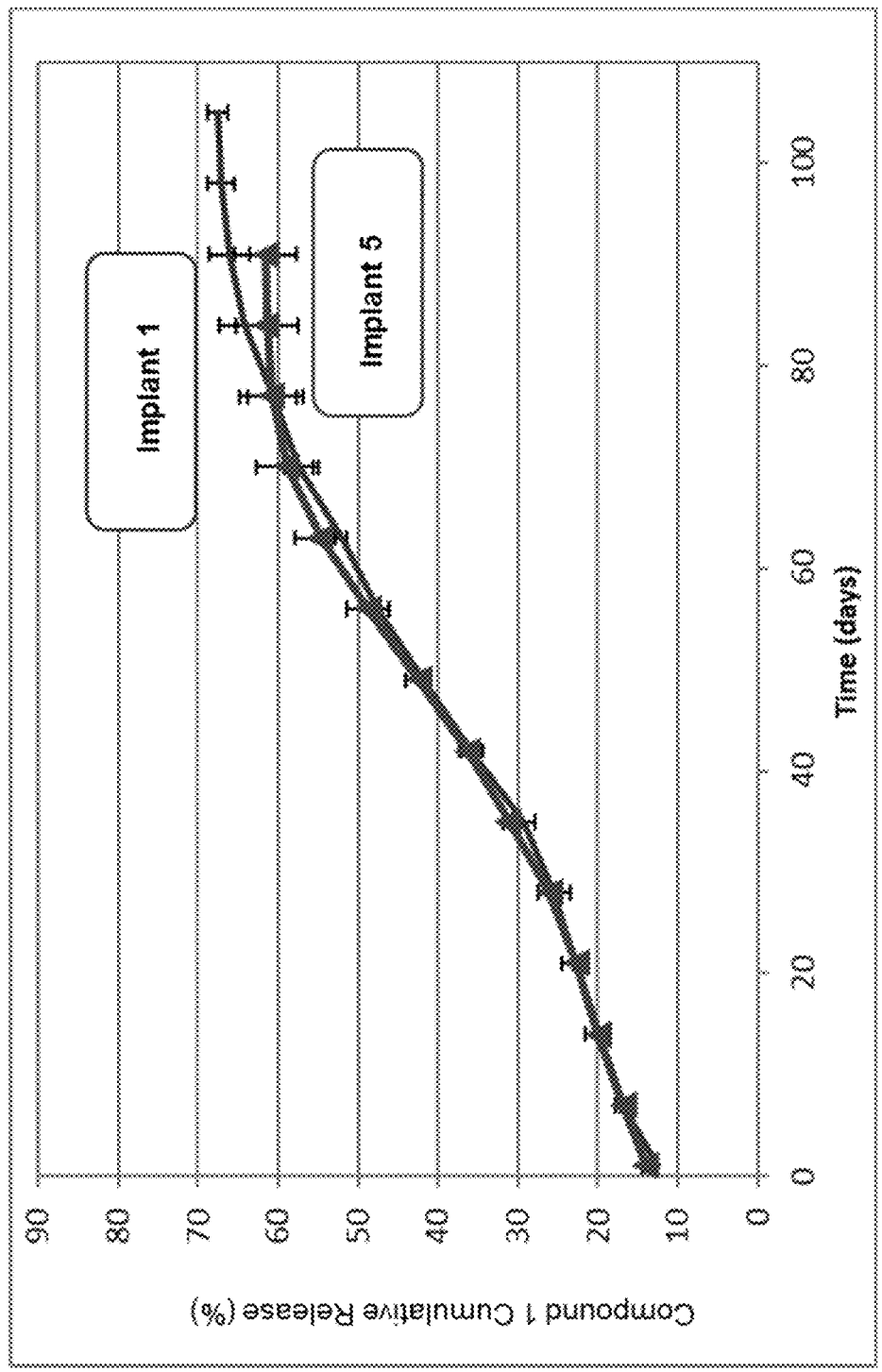
FIG. 4 shows the in vitro cumulative total percent release of Compound 1 into phosphate buffered saline (0.01 M; pH 7.4) at 37° C. over time for Implants 1 and 5. The composition of each implant is set forth in Table 2.
Figure 5:
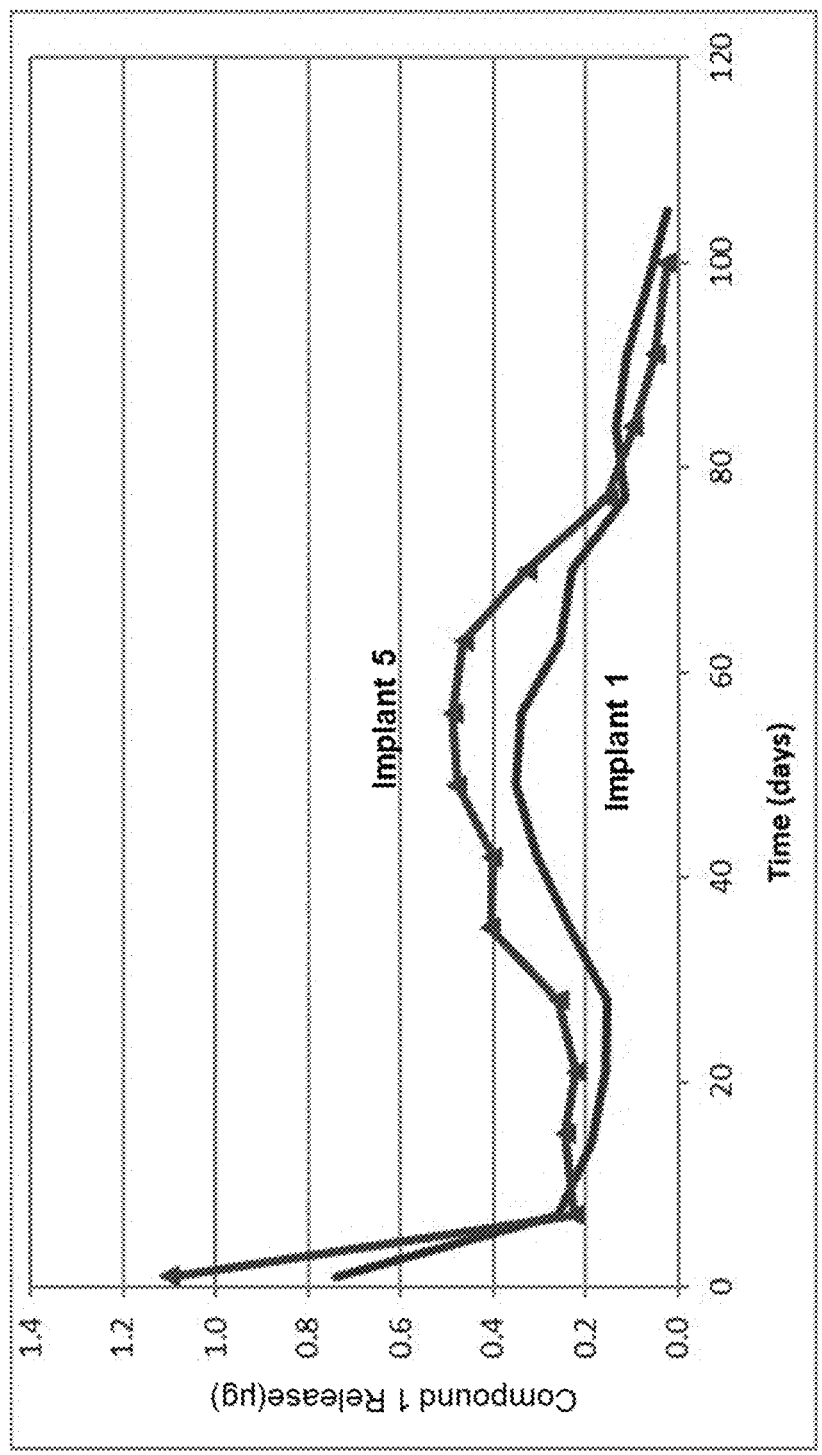
FIG. 5 shows the in vitro daily release rate of Compound 1 into phosphate buffered saline (0.01 M; pH 7.4) at 37° C. over time for Implants 1 and 5. The composition of each implant is set forth in Table 2.
Figure 6:
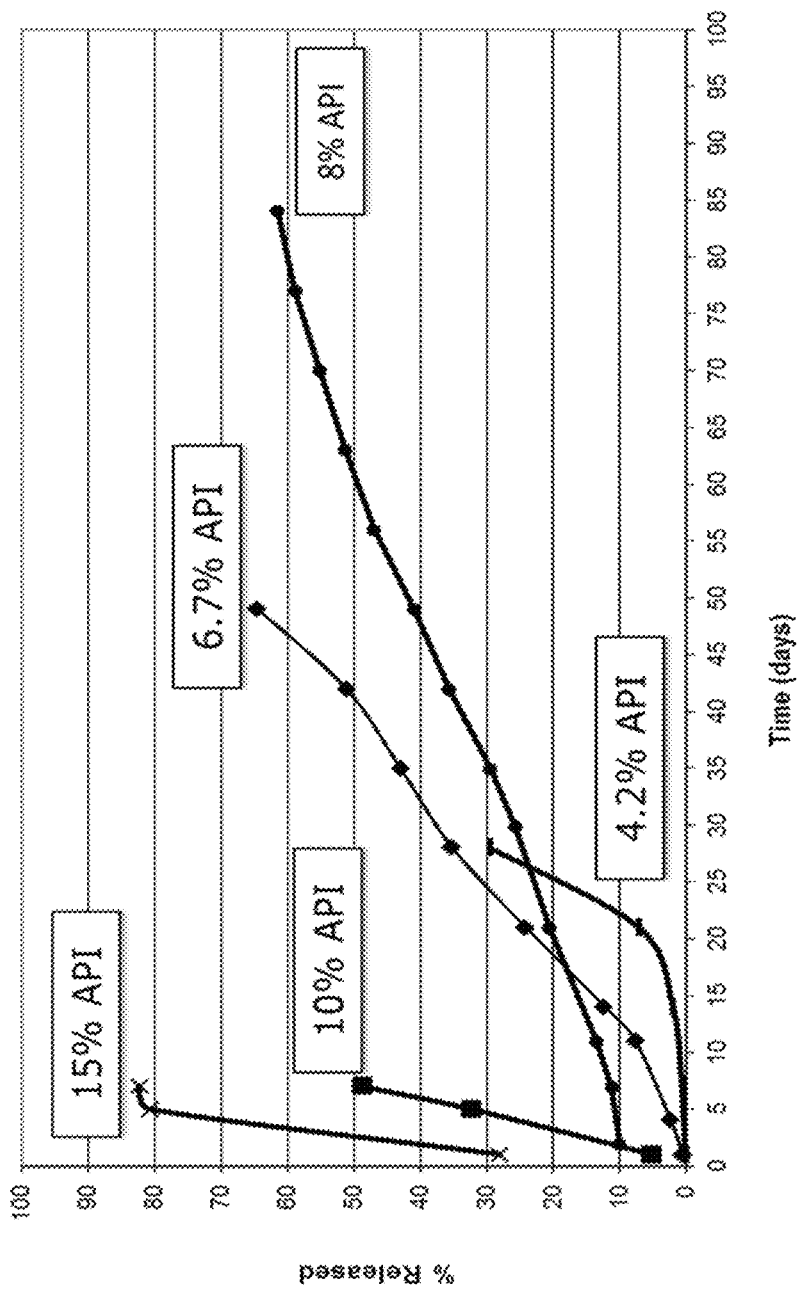
FIG. 6 shows the in vitro cumulative total percent release of Compound 1 (API) in implants of R202H at different loadings (wt %) of Compound 1.

The drug-release profiles for the implants of Table 2 extruded under the conditions specified in Table 1 are shown in FIGS. 2 and 3. The figure also includes Implant 1 formulation comprising 8 wt % Compound 1 as a comparative implant. Data points represent the average release of 3 replicate implant samples not normalized to their relative weight. Implant 5, 15% drug loading, has similar release profile as Implant 1 (FIG. 4), and the daily release rate is similar to or higher than Implant 1 (FIG. 5) with less than 30% release of compound 1 on day 1. However, implant 5 showed this lack of a burst release while being able to contain almost double the amount of Compound 1 in the implant. As can be seen by comparison to implants made with just R202H as the polymer (FIG. 6), the implants of Table 2 showed better release profiles in that they did not show the initial burst release seen with drug loadings of greater than 8% (w/w) in the R202H implants. For example, as seen in FIG. 6, when only R202H was used as opposed to the polymer mixtures of Table 2 in an implant with 15% drug loading, the release rate on day 1 was approximately 28%; on the other hand, as can be seen in FIGS. 3 and 4, implants 4 and 5 (both also with 15% drug loading) showed release rates on day 1 of about 12%. In addition, see also U.S. Pat. No. 9,889,142 which also shows burst release in implants with loadings above 8%, which can be as high as about 55% drug release on day 1).

Based on the above, it can be seen that with the implant formulations described herein, a similar acceptable drug release profile can be seen as with the 8 wt % implants (e.g. a fairly steady release with no initial burst release), but the present implants show this acceptable release at drug loadings significantly higher than 8 wt % (e.g. 15 wt %).

Example 3

Implant Swelling

Figure 8:
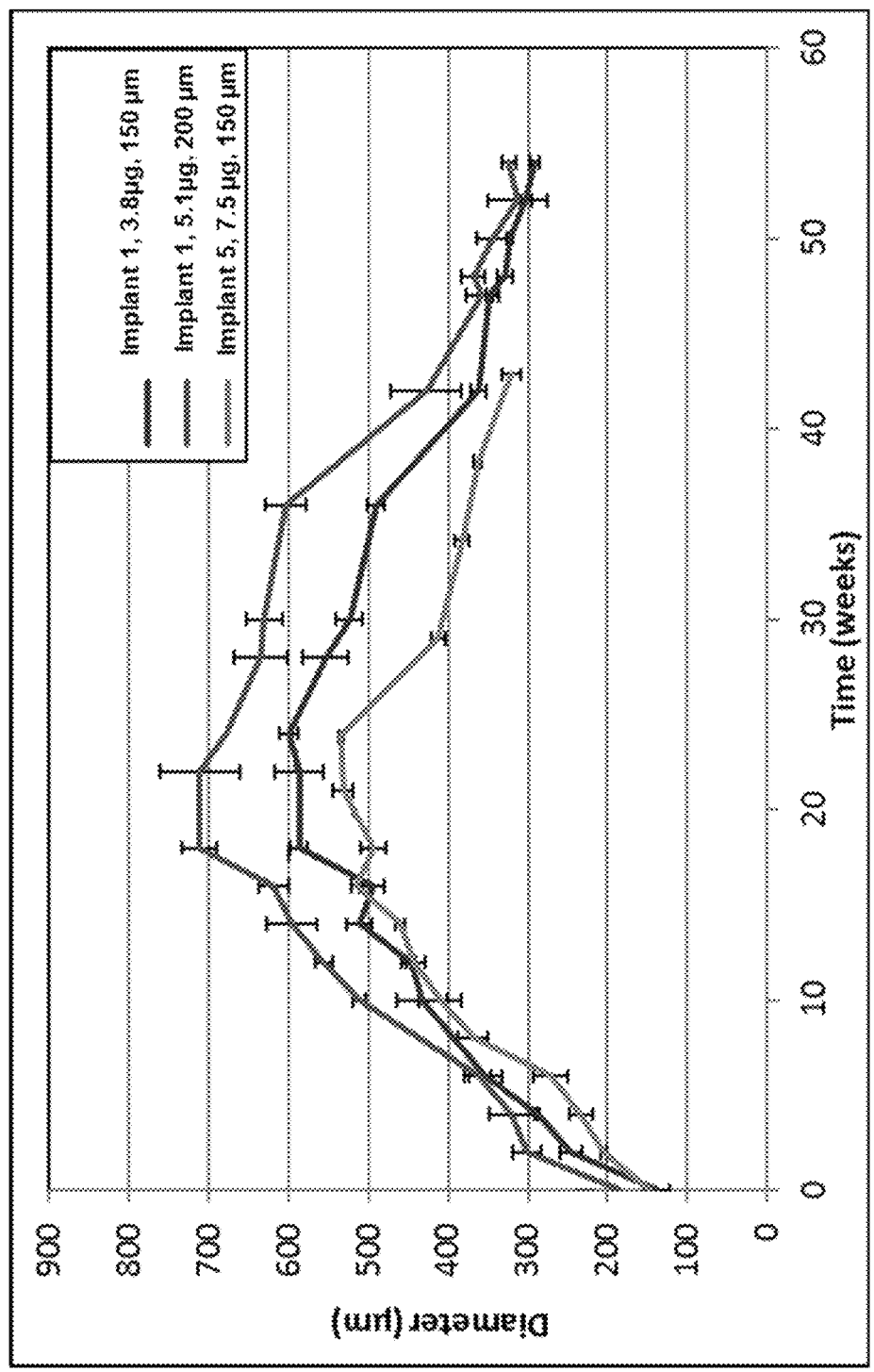
FIG. 8 shows swelling study results for Implants 1 and 5 by a graph.

Swelling study was conducted per the polymer implant swelling work instruction guide. Physical appearance and dimensional measurement of samples of the implants were studied using a Keyence digital microscope (Model VHX-600). Images were acquired at 100× and 150× magnifications for the extruded implants. The medium used for this study was 0.01 M PBS, pH 7.4, 37° C. The swelling behavior of all implants is summarized in FIG. 7. A comparison of the maximum swelling diameter of Implant 1 and Implant 5 is shown in FIG. 8. The implant 5 maximum swell diameter is less than the Implant 1 maximum swell diameter, with the maximum swell diameter of Implant 5 being about 75% to about 85% the maximum swell diameter of Implant 1.

Example 4

In Vitro Polymer Degradation

In vitro polymer life-time of Implant 2 to 6 were compared with Implant 1. The study was performed in aqueous buffer solution (0.01M PBS, pH 7.4) at 37° C. for 24 weeks. The degradation rate constants were estimated by fitting the decrease of the average molecular weights ($MW_{peak}$) of the polymeric matrices over time to a first order kinetics. The rank order of the formulations based on the total kinetic rate constants and the estimated in vitro lifetimes ($t_{1000}$, which is the time to reach a $MW_{peak}$ of 1000 g/mol) are summarized in Table 3. The reported molecular weight data was relative to polystyrene standards.

TABLE 3

The experimental rate constants (k) for polymer degradation, the estimated in vitro life-time and the predicted in vivo life-time

| Implant No | % Drug Loading | k (37° C.) (1/day) | Initial MW (M0) | In vitro t1000 (Month) | In vivo Life-time (Month) |
| --- | --- | --- | --- | --- | --- |
| 1 | 8 | 0.00963 | 18200 | 9.9 | 14.1 |
| 2 | 12 | 0.01039 | 15650 | 8.7 | 12.4 |
| 3 | 12 | 0.01060 | 16700 | 8.7 | 12.4 |
| 4 | 15 | 0.01146 | 16000 | 8.0 | 11.3 |
| 5 | 15 | 0.01230 | 16500 | 7.5 | 10.6 |
| 6 | 11 | 0.01303 | 16350 | 7.1 | 10.0 |

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A biodegradable intraocular implant comprising about 15% by weight of Compound 1:

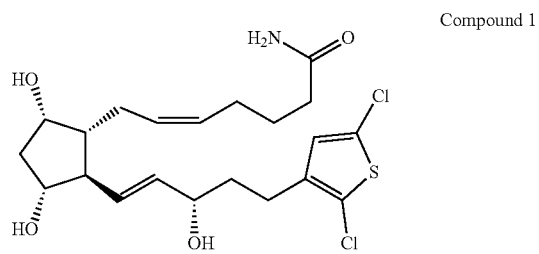 [SMILES: NC(=O)CCC/C=C\C[C@@H]1[C@@H](/C=C/[C@@H](O)CCc2cc(Cl)sc2Cl)[C@H](O)C[C@@H]1O]

Compound 1 about 5% by weight of a first polymer that is poly(D,L-lactide) having an acid end group and an inherent viscosity of about 0.16-0.24 dl/g, about 30% by weight of a second polymer that is poly(D,L-lactide) having an ester end group and an inherent viscosity of about 0.25-0.35 dl/g, about 45% by weight of a third polymer that is poly(D,L-lactide-co-glycolide) having an ester end group and an inherent viscosity of about 0.16-0.24 dl/g and a D,L-lactide:glycolide ratio of about 75:25, about 3% by weight cetyl alcohol, and about 2% by weight butylated hydroxyanisole, wherein the inherent viscosities of the first, second, and third polymers correspond to those measured for a 0.1% solution of the polymer in chloroform at 25° C.;

and wherein the implant releases in vitro less than 30% of Compound 1 during the first 24 hours wherein the in vitro release of Compound 1 is measured in a phosphate buffered saline (PBS) solution at a pH of 7.4±0.05 and at 37° C., and wherein the PBS solution is a PBS solution that is free of magnesium and calcium and has a pH of 7.4±0.05 at 25° C.

2. The biodegradable intraocular implant of claim 1, wherein the implant releases in vitro less than 20% of Compound 1 during the first 24 hours.

3. The biodegradable intraocular implant of claim 1, wherein the implant releases in vitro less than 15% of Compound 1 during the first 24 hours.

4. The biodegradable intraocular implant of claim 1, wherein the implant is sized for placement in the anterior chamber of the eye.

5. The biodegradable intraocular implant of claim 1, wherein the diameter of the implant is about 150 μm and the implant contains about 5 μg or about 7.5 μg of Compound 1.

6. The biodegradable intraocular implant of claim 1, wherein the diameter of the implant is about 200 μm and the implant contains about 5μg or about 7.5 μg of Compound 1.

* * * * *